United States Patent
Self et al.

(10) Patent No.: US 9,950,007 B2
(45) Date of Patent: Apr. 24, 2018

(54) NEURONAL PROTECTION BY CERIUM OXIDE NANOPARTICLES

(71) Applicant: UNIVERSITY OF CENTRAL FLORIDA RESEARCH FOUNDATION, INC., Orlando, FL (US)

(72) Inventors: William T. Self, Oviedo, FL (US); Ella Bossy-Wetzel, Winter Park, FL (US); Sudipta Seal, Orlando, FL (US); Janet Dowding, Winter Garden, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 57 days.

(21) Appl. No.: 14/733,185

(22) Filed: Jun. 8, 2015

(65) Prior Publication Data
US 2016/0038537 A1  Feb. 11, 2016

Related U.S. Application Data

(62) Division of application No. 13/624,485, filed on Sep. 21, 2012, now Pat. No. 9,161,950.

(60) Provisional application No. 61/537,368, filed on Sep. 21, 2011.

(51) Int. Cl.
A61K 33/24 (2006.01)

(52) U.S. Cl.
CPC .................... A61K 33/24 (2013.01)

(58) Field of Classification Search
None
See application file for complete search history.

(56) References Cited

U.S. PATENT DOCUMENTS

| | | |
|---|---|---|
| 5,089,860 A | 2/1992 | Deppe et al. |
| 5,411,647 A | 5/1995 | Johnson et al. |
| 5,486,359 A | 1/1996 | Caplan et al. |
| 5,910,311 A | 6/1999 | Boussourira |
| 5,961,993 A | 10/1999 | Boussourira |
| 6,042,714 A | 3/2000 | Lin et al. |
| 6,103,247 A | 8/2000 | Boussourira |
| 6,139,985 A | 10/2000 | Borglum et al. |
| 6,316,012 B1 | 11/2001 | N'Guyen |
| 6,327,074 B1 | 12/2001 | Bass et al. |
| 6,368,577 B1 | 4/2002 | Kropf et al. |
| 6,406,685 B1 | 6/2002 | Philippe |
| 6,468,551 B1 | 10/2002 | Diec |
| 6,497,863 B1 | 12/2002 | Wachter |
| 6,497,875 B1 | 12/2002 | Griesbach |
| 6,501,590 B2 | 12/2002 | Bass et al. |
| 6,592,746 B1 | 7/2003 | Schmid-Schoenbein et al. |
| 6,654,161 B2 | 11/2003 | Bass et al. |
| 6,844,387 B2 | 1/2005 | Bass et al. |
| 6,890,896 B1 | 5/2005 | Shashoua |
| 7,005,504 B2 | 2/2006 | Hsei et al. |
| 7,075,707 B1 | 7/2006 | Rapaport et al. |
| 7,141,227 B2 | 11/2006 | Chan |
| 7,270,813 B2 | 9/2007 | Shimp et al. |
| 7,347,987 B2 | 3/2008 | McGinnis et al. |
| 7,431,758 B2 | 10/2008 | Ota et al. |
| 7,442,686 B2 | 10/2008 | Lasko et al. |
| 7,471,706 B2 | 12/2008 | Bass et al. |
| 7,504,356 B1 | 3/2009 | Self et al. |
| 7,507,480 B2 | 3/2009 | Sugaya |
| 7,534,453 B1 | 5/2009 | Rzigalinski et al. |
| 7,563,459 B2 | 7/2009 | Phillips et al. |
| 7,642,250 B2 | 1/2010 | Williams |
| 7,687,505 B2 | 3/2010 | Sugaya |
| 7,725,802 B2 | 5/2010 | Katusic et al. |
| 7,772,375 B2 | 8/2010 | Greferath et al. |
| 7,888,119 B2 | 2/2011 | Sugaya et al. |
| 7,899,093 B1 | 3/2011 | Bass et al. |
| 7,906,147 B2 | 3/2011 | Hainfield et al. |
| 7,924,617 B2 | 4/2011 | Yadav |
| 8,080,420 B2 | 12/2011 | Sugaya |
| 8,097,270 B2 | 1/2012 | Ketelson et al. |
| 8,172,901 B2 | 5/2012 | Goulet et al. |
| 2003/0050709 A1 | 3/2003 | Noth et al. |
| 2003/0187077 A1 | 10/2003 | Chane-Ching |
| 2003/0228277 A1 | 12/2003 | Gehlsen |
| 2004/0013658 A1 | 1/2004 | Fulton et al. |
| 2004/0048808 A1 | 3/2004 | Hamdi et al. |
| 2004/0062753 A1 | 4/2004 | Rezania et al. |

(Continued)

FOREIGN PATENT DOCUMENTS

| | | |
|---|---|---|
| WO | WO 1999/015891 | 4/1999 |
| WO | WO 2003/059263 A2 | 7/2003 |

(Continued)

OTHER PUBLICATIONS

Estevez et al. "Neuroprotective mechanisms of cerium oxide nanoparticles in a mouse hippocampal brain slice model of ischemia" 2011.*
Becker et a. "Risk of stroke in patients with idiopathic Parkinson disease". 2010.*
Perl "Neuropathology of Alzheimer's Disease" 2010.*
Rzigalinski "Cerium Oxide nanoparticles in Treatment of Parkinsons' Disease". 2009.*
Miranda S, et al. (2000) "The role of oxidative stress in the toxicity induced by amyloid [beta]-peptide in Alzheimer's disease." Progress in Neurobiology, vol. 62(6): pp. 633-648.
Kayed R, et al. (2003) "Common structure of soluble amyloid oligomers implies common mechanism of pathogenesis." (Translated from eng) Science, vol. 300(5618): pp. 486-489 (in eng).
Pietraforte D, et al, (2003) "Peroxynitrite-dependent modifications of tyrosine residues in hemoglobin. Formation of tyrosyl radical(s) and 3-nitrotyrosine." (Translated from eng) Amino Acids, vol. 25(3-4): pp. 341-350 (in eng).
Radi R, et al, (2001) "Unraveling peroxynitrite formation in biological systems." (Translated from eng) Free Radic Biol Med, vol. 30(5): pp. 463-488 (in eng).

(Continued)

*Primary Examiner* — Robert A Wax
*Assistant Examiner* — Danah Al-Awadi
(74) *Attorney, Agent, or Firm* — Timothy H. Van Dyke; Beusse, Wolter, Sanks & Maire PLLC

(57) ABSTRACT

A method of treating a subject with elevated levels of peroxynitrite includes administering a therapeutically effective amount of cerium oxide nanoparticles to the subject, wherein the cerium oxide nanoparticles reduce the level of peroxynitrite in the subject.

7 Claims, 12 Drawing Sheets

(56) References Cited

U.S. PATENT DOCUMENTS

| | | |
|---|---|---|
| 2005/0159820 A1 | 7/2005 | Yoshikawa et al. |
| 2005/0164377 A1 | 7/2005 | Miyabayashi et al. |
| 2005/0171192 A1 | 8/2005 | Gehlsen |
| 2006/0110440 A1 | 5/2006 | Sugaya et al. |
| 2006/0134789 A1 | 6/2006 | Sugaya et al. |
| 2006/0141137 A1 | 6/2006 | Anderson et al. |
| 2006/0280729 A1 | 12/2006 | Mistry |
| 2007/0003621 A1 | 1/2007 | Nagia et al. |
| 2007/0072825 A1 | 3/2007 | Williams |
| 2007/0123996 A1 | 5/2007 | Sugaya et al. |
| 2009/0087493 A1 | 4/2009 | Dai et al. |
| 2009/0098574 A1 | 4/2009 | Brisson et al. |
| 2009/0269410 A1 | 10/2009 | McGinnis et al. |
| 2010/0098768 A1 | 4/2010 | Andreescu et al. |
| 2010/0151000 A1 | 6/2010 | Thomas et al. |
| 2010/0247428 A1 | 9/2010 | Kim et al. |

FOREIGN PATENT DOCUMENTS

| | | |
|---|---|---|
| WO | WO 2006/118954 A2 | 11/2006 |
| WO | WO 2007/002662 A2 | 1/2007 |
| WO | 2008064357 A2 | 5/2008 |
| WO | WO 2008/064357 A2 | 5/2008 |
| WO | WO 2009/132277 A1 | 10/2009 |

OTHER PUBLICATIONS

Ye YZ. et al. (1996) "Antibodies that recognize nitrotyrosine." (Translated from eng) Methods Enzymol, vol. 269: pp. 201-209 (in eng).

Besancon E, et al. (2008) "Beyond NMDA and AMPA glutamate receptors: emerging mechanisms for Ionic imbalance and cell death in stroke." (Translated from eng) Trends Pharmacol Sci, vol. 29(5): pp. 268-275 (in eng).

Smith DG, et al, (2007) "The redox chemistry of the Alzheimer's disease amyloid beta peptide." Translated from eng) Biochim Biophys Acta, vol. 1768(8): pp. 1976-1990 (in eng).

Zhang YJ, et al, (2005) "Nitration and oligomerization of tau induced by peroxynitrite inhibit its microtubule-binding activity." (Translated from English) Febs Lett, vol. 579(11): pp. 2421-2427 (in English).

Crow JP, et al. (1997) "Superoxide dismutase catalyzes nitration of tyrosines by peroxynitrite in the rod and head domains of neurofilament-L." (Translated from eng) J Neurochem vol. 69(5): pp. 1945-1953 (in eng).

Tohgi H, et al. (1999) "Alterations of 3-nitrotyrosine concentration in the cerebrospinal fluid during aging and in patients with Alzheimer's disease." (Translated from eng) Neurosci Lett, vol. 269(1): pp. 52-54 (in eng).

Basso M, et al. (2009) "Characterization of Detergent-Insoluble Proteins in ALS Indicates a Causal Link between Nitrative Stress and Aggregation in Pathogenesis." PLoS One, vol. 4(12): pp. e8130.

Bishop A, et al. (2009) "Differential sensitivity of oligodendrocytes and motor neurons to reactive nitrogen species: implications for multiple sclerosis." (Translated from eng) J Neurochem, vol. 109(1): pp. 93-104 (in eng).

Ischiropoulos H & Beckman JS (2003) "Oxidative stress and nitration in neurodegeneration: cause, effect, or association?" (Translated from eng) J Clin Invest, vol. 111(2): pp. 163-169 (in eng).

Torreilles F, et al, (1999) "Neurodegenerative disorders: the role of peroxynitrite." (Translated from eng) Brain Res Brain Res Rev, vol. 30(2): pp. 153-163 (in eng).

Alkam T, et al. (2008) "The extensive nitration of neurofilament light chain in the hippocampus is associated with the cognitive impairment induced by amyloid beta in mice." (Translated from eng) J Pharmacol Exp Ther, vol. 327(1): pp. 137-147 (in eng).

Bonte FJ, et al, (Jul. 2006). "Tc-99m HMPAO SPECT in the differential diagnosis of the dementias with histopathologic confirmation". Clin Nucl Med, vol. 31 (7): pp. 376-378.

Dougall NJ, et al, (2004). "Systematic review of the diagnostic accuracy of 99mTc-HMPAO-SPECT in dementia". Am J Geriatr Psychiatry, vol. 12 (6): pp. 554-570.

De Meyer G, et al, (Aug. 2010). "Diagnosis-Independent Alzheimer Disease Biomarker Signature in Cognitively Normal Elderly People". Arch Neurol., vol. 67 (8): pp. 949-956.

Martinez-Ruiz A, et al. "Nitric oxide signalling: classical, less classical, and nonclassical mechanisms." Free Radic Biol Med. vol. 2011; 51: pp. 17-29.

Stamler JS, et al, "Nitrosylation. the prototypic redox-based signaling mechanism." Cell. 2001: vol. 106(6): pp. 675-683.

Ghatan S, et al. "p38 MAP kinase mediates bax translocation in nitric oxide-induced epoptosis in neurons." J Cell Biol. 2000; vol. 150: pp. 335-347.

Knott AB, et al, "Mitochondrial fragmentation in neurodegeneration." Nat Rev Neurosci. 2008; vol. 9: pp. 505-518.

Manczak M. et al, "Impaired mitochondrial dynamics and abnormal interaction of amyloid beta with mitochondrial protein Drp1 in neurons from patients with Alzheimer's disease: implications for neuronal damage." Hum Mol Genet. 2011; vol. 20: pp. 2495-2509.

Ikiz B, et al, "A sequel to the tale of p25/Cdk5 in neurodegeneration." Neuron. 2008 ; vol. 60: pp. 731-732.

Swerdlow RH. "Pathogenesis of Alzheimer's disease." Clin Interv Aging. 2007; vol. 2: pp. 347-359.

Chaturvedi RK, et al, "Mitochondrial approaches for neuroprotection." Ann N Y Acad Sci. 2008; vol. 1147: pp. 395-412.

Estevez AY, et al. "Neuroprotective mechanisms of cerium oxide nanoparticles in a mouse hippocampal brain slice model of ischemia." Free Radic Biol Med. 2011; vol. 51: pp. 1155-1163.

Song W, et al. "Assessing mitochondrial morphology and dynamics using fluorescence wide-field microscopy and 3D image processing." Methods. 2008; vol. 46: pp. 295-303.

Bossy-Wetzel E, et al. "Crosstalk between nitric oxide and zinc pathways to neuronal cell death involving mitochondrial dysfunction and p38-activated K+ channels." Neuron. 2004; vol. 41: pp. 351-365.

Knott AB, et al "Impact of nitric oxide on metabolism in health and age-related disease." Diabetes Obes Metab. 2010: vol. 12: pp. 126-133.

Bossy B, et al, "S-Nitrosylation of DRP1 does not affect enzymatic activity and is not specific to Alzheimer's disease." J Alzheimers Dis. 2010: vol. 20 Suppl 2: pp. S513-S526.

Wang X, et al. "impaired balance of mitochondrial fission and fusion in Alzheimer's disease." J Neurosci. 2009; vol. 29: pp. 9090-9103.

Taguchi N, et al "Mitotic phosphorylation of dynamin-related GTPase Drp1 participates in mitochondrial fission." J Biol Chem. 2007; vol. 282: pp. 11521-1152.

Yamano K, et al, "Coupling mitochondrial and cell division." Nat Cell Biol. 2011; vol. 13: pp. 1026-1027.

Nguyen MD, et al, "Cycling at the interface between neurodevelopment and neurodegeneration." Cell Death Differ, 2002; vol. 9: pp. 1294-1306.

Crews L, et al, "Molecular mechanisms of neurodegeneration in Alzheimer's disease." Hum Mol Genet. 2010; vol. 19: pp. R12-R20.

Qu J, et al, "S-Nitrosylation activates Cdk5 and contributes to synaptic spine loss induced by beta-amyloid peptide." Proc Natl Acad Sci U S A. 2011; vol. 108: pp. 14330-14335.

Knott AB, et al, "Nitric oxide in health and disease of the nervous system." Antioxid Redox Signal. 2009; vol. 11: pp. 541-554.

Swerdlow RH, et al, "The Alzheimer's disease mitochondrial cascade hypothesis." J Alzheimers Dis. 2010; vol. 20 Suppl 2: pp. S265-S279.

Chan DC. "Mitochondria: dynamic organelles in disease, aging, and development." Cell. 2006; vol. 125: pp. 1241-1252.

Drisko, J.A. et al., "The use of Antioxidants with First-Line Chemotherapy in Two Cases of Ovarian Cancer", J Am Coll Nut, 2003, vol. 22(2), pp. 118-123.

Korsvik et al., "Superoxide dismutase mimetic properties exhibited by vacancy engineered ceria nanoparticles", Chem. Commun., 2007, pp. 1056-1058.

(56) References Cited

OTHER PUBLICATIONS

Yu et al., "Large-scale nonhydrolytic sol-gel synthesis of uniform-sized ceria nanocrystals with spherical, wire, and tadpole shapes", Angew. Chem. Int. Ed., 2005, vol. 44, pp. 7411-7414.
Ahluwalia et al., "Critical role of hypoxia sensor-HIF1 alpha in VEGF gene activation, implication for angiogenesis and tissue injury healing", Current Medicinal Chemistry, 2012, vol. 19, p. 94.
Perez, J.M. et al., "Synthesis of Biocompatible Dextran-Coated Nanoceria with pH-Dependent Antioxidant Properties", 2008, Small, vol. 4, No. 5, pp. 552-556.
Griffiths, J.R., "Are Cancer Cells Acidic?", British Journal of Cancer, 1991, vol. 64, pp. 425-427.
De Wever, O. et al., "Stromal myofibroblasts are drivers of invasive cancer growth", International Journal of Cancer, 2008, vol. 123, pp. 2229-2238.
Lam, M.A., et al., "Nitric Oxide and Nitroxides Can Act as Efficient Scavengers of Protein-Derived Free Radicals", Chem Res. Toxicol, 2008, vol. 21, pp. 2111-2119.
Karakoti, A.S., et al., "Nanoceria as Antioxidant: Synthesis and Biomedical Applications", JOM, 2008, vol. 60(3), pp. 33-37.
Clinicaltrials.gov, "Clinical Trial for the Treatment of Diabetic Foot Ulcers Using a Nitric Oxide Releasing Patch: PATHON", (http://web.archive.org/web/20091130234819/http://clinicaltrials.gov/show/NCT/00428727) published online Nov. 30, 2009.
Deshpande et al., "Size dependency variation in lattice parameter and valency states in nanocrystalline cerium oxides", Appl;ied Physics Letters, 2005, vol. 87, pp. 133113-1-133113-3.
Rasmussen et al., "Penetration of intact skin by quantum dots with diverse physiochemical properties", Toxicological Sciences, 2006, vol. 91, pp. 159-165.
Park et al., "Oxidative stress induced by cerium oxide nanoparticles in cultured BEAS-2B cells", Toxicology, 2008, vol. 245, pp. 90-100.
MSDS from Aldrich for cerium oxide powder bulk product, Feb. 2013, 6 pages.
Kuchibhatla, S. et al., "Hierarchicial assembly of inorganic nanostructure building blocks to octahedral superstructures—atrue template-free self-assembly", Nanotechnology, 2007, vol. 17 pp. 1-4.
Kuchibhatla, S, "Probing and Tuning the Size, Morphology, Chemistry and Structure of Nanoscale Cerium Oxide", Diss. University of Central Florida, 2008, 175 pages.
Giri, S et al., "Nanoceria: A Rare-Earth Nanoparticle as a Novel Anti-Angiogenic Therapeutic Agent in Ovarian Cancer", PLOS ONE, Jan. 2013, vol. 8, Issue 1, e54578.
Bossy-Wetzel E, et al, (2004) "Molecular pathways to neurodegeneration." (Translated from eng) Nat Med 10 Suppl:vol. S, pp. 2-9 (in eng).
Ferri CP, et al. (2005) "Global prevalence of dementia: a Delphi consensus study." (Translated from eng) Lancet. vol. 366(9503): pp. 2112-2117 (in eng).
Markesbery WR (1997) "Oxidative stress hypothesis in Alzheimer's disease." (Translated from eng) Free Radic Biol Med, vol. 23(1): pp. 134-147 (in eng).
Pacher P, et al, (2007) "Nitric oxide and peroxynitrite in health and disease." (Translated from eng) Physiol Rev, vol. 87(1): pp. 315-424 (in eng).
Barsoum MJ, et al. (2006) "Nitric oxide-induced mitochondrial fission is regulated by dynamin-related GTPases in neurons." (Translated from eng) EMBO J vol. 25(16): pp. 3900-3911 (in eng).
Smith MA, et al, (1997) "Widespread peroxynitrite-mediated damage in Alzheimer's disease." (Translated from eng) J Neurosci, vol. 17(8): pp. 2653-2657 (in eng).
Texel SJ & Mattson MP (2011) "Impaired adaptive cellular responses to oxidative stress and the pathogenesis of Alzheimer's disease." (Translated from eng) Antioxid Redox Signal, vol. 14(8): pp. 1519-1534 (in eng).
Boczkowski J, et al. (2001) "Peroxynitrite-mediated mitochondrial dysfunction." (Translated from eng) Biol Signals Recept, vol. 10(1-2): pp. 66-80 (in eng).

Shankar GM, et al. (2007) "Natural oligomers of the Alzheimer amyloid-beta protein induce reversible synapse loss by modulating an NMDA-type glutamate receptor-dependent signaling pathway." (Translated from eng) J Neurosci, vol. 27(11): pp. 2866-2875 (in eng).
Reynolds MR, et al. (2006) "Tau nitration occurs at tyrosine 29 in the fibrillar lesions of Alzheimer's disease and other tauopathies." (Translated from eng) J Neurosci. vol. 26(42): pp. 10636-10645 (in eng).
Reyes JF, et al. (2008) "A possible link between astrocyte activation and tau nitration in Alzheimer's disease." (Translated from English) Neurobiol Dis, vol. 31(2): pp. 198-208 (in English).
Cadenas E & Boveris A (2005) "Mitochondrial Free Radical Production, Antioxidant Defenses and Cell Signalling." Reactions, Processes, The Handbook of Environmental Chemistry, ed Grune T (Springer Berlin / Heidelberg), vol. 2O, pp. 615-643.
Mattson MP, (2008) "Mitochondria in neuroplasticity and neurological disorders." (Translated from eng) Neuron, vol. 60(5): pp. 748-766 (in eng).
Rabkin SW, et al, (2008) "Metalloporphyrins as a therapeutic drug class against peroxynitrite in cardiovascular diseases involving ischemic reperfusion injury." (Translated from eng) Eur J Pharmacol, vol. 586: pp. (1-3):1-8 (in eng).
Rong Y, et al, (1999) "EUK-134, a synthetic superoxide dismutase and catalase mimetic, prevents oxidative stress and attenuates kainate-induced neuropathology." (Translated from eng) Proc Natl Acad Sci U S A, vol. 96(17): pp. 9897-9902 (in eng).
Sharpe MA, et al, (2002) "Oxidation of nitric oxide by oxomanganese-salen complexes: a new mechanism for cellular protection by superoxide dismutase/catalase rnimetics." (Translated from eng) Biochem J, vol. 366(Pt 1): pp. 97-107 (in eng).
van Empel VP, et al. (2006) "EUK-8, a superoxide dismutase and catalase mimetic, reduces cardiac oxidative stress and ameliorates pressure overload-induced heart failure in the harlequin mouse mutant." (Translated from eng) J Am Coll Cardiol, vol. 48(4): pp. 824-832 (in eng).
Celardo I, et al, (2011) "Pharmacological potential of cerium oxide nanoparticles." (Translated from eng) Nanoscale, vol. 3(4): pp. 1411-1420 (in eng).
Chen J, et al, (2006) "Rare earth nanoparticles prevent retinal degeneration induced by intracellular peroxides." (Translated from eng) Nat Nanotechnol, vol. 1(2): pp. 142-150 (in eng).
Karakoti A, et al, (2010) "Redox-active radical scavenging nanomaterials." (Translated from eng) Chem Soc Rev, vol. 39(11): pp. 4422-4432 (in eng).
Heckert EG, et al, (2008) "The role of cerlum redox state in the SOD mimetic activity of nanoceria." (Translated from eng) Biomaterials, vol. 29(18): pp. 2705-2709 (in eng).
Korsvik C, et al, (2007) "Superoxide dismutase mimetic properties exhibited by vacancy engineered ceria nanoparticles." (Translated from English) Chem Commun, vol. (10): pp. 1056-1058 (in English).
Pirmohamed T, et al. (2010) "Nanoceria exhibit redox state-dependent catalase mimetic activity." (Translated from eng) Chem Commun (Camb). vol. 46(16): pp. 2736-2738 (in eng).
Anonymous (2009) "Cerium Oxide Nanoparticles Trigger Neuronal Survival in a Human Alzheimer Disease Model by Modulating BDNF Pathway." Current Nanoscience, vol. 5: pp. 167-176.
Das M, et al. (2007) "Auto-catalytic ceria nanoparticles offer neuroprotection to adult rat spinal cord neurons." (Translated from eng) Biomaterials, vol. 28(10): pp. 1918-1925 (in eng).
Schubert D, et al, (2006) "Cerium and yttrium oxide nanoparticles are neuroprotective." (Translated from eng) Biochem Biophys Res Commun, vol. 342(1): pp. 86-91 (in eng).
Hardas SS, et al. (2010) "Brain distribution and toxicological evaluation of a systemically delivered engineered nanoscale ceria." (Translated from eng) Toxicol Sci, vol. 116(2): pp. 562-576 (in eng).
Hirst SM, et al. (2011) "Bio-distribution and in vivo antioxidant effects of cerium oxide nanoparticles in mice." (Translated from Eng) Environ Toxicol (in Eng).
Beckman JS (2009) "Understanding peroxynitrite biochemistry and its potential for treating human diseases." (Translated from eng) Arch Biochem Biophys, vol. 484(2): pp. 114-116 (in eng).

(56) References Cited

OTHER PUBLICATIONS

Liot G, et al. (2009) "Complex II Inhibition by 3-NP causes mitochondrial fragmentation and neuronal cell death via an NMDA- and ROS-dependent pathway." (Translated from eng) Cell Death Differ, vol. 16(6): pp. 899-909 (in eng).
Viera L, et al, (1999) "Immunohistochemical methods to detect nitrotyrosine." (Translated from eng) Methods Enzymol, vol. 301: pp. 373-381 (in eng).
Patil S, et al, (2002) "Synthesis of Nanocrystalline Ceria Particles for High Temperature Oxidation Resistant Coating." Journal of Nanoparticle Research, vol. 4(5): pp. 433-438.
Mailander V, et al, (2009) "Interaction of nanoparticles with cells." (Translated from eng) Biomacromolecules, vol. 10(9): pp. 2379-2400 (in eng).
Vincent A, et al. (2009) "Protonated nanoparticle surface governing ligand tethering and cellular targeting." (Translated from eng) ACS Nano, vol. 3(5): pp. 1203-1211 (in eng).
Limbach LK, et al. (2005) "Oxide nanoparticle uptake in human lung fibroblasts: effect of particle size, agglomeration and diffusion at low concentrations." (Translated from eng) Environ Sci Technol, vol. 39(23): pp. 9370-9376 (in eng).
Owens DE, et al, (2006) "Opsonization, biodistribution, and pharmacokinetics of polymeric nanoparticles." (Translated from eng) Int J Pharm, vol. 307(1): pp. 93-102 (in eng).
Radi R (1996) "Kinetic analysis of reactivity or peroxynitrite with biomolecules." (Translated from eng) Methods Enzymol, vol. 269: pp. 354-366 (in eng).
Lymar SV, et al (1995) "Rapid reaction between peroxynitrite ion and carbon dioxide: Implications for biological activity," Journal of the American Chemical Society, vol. 117(34): pp. 8867-8868.
Pompella A. et al (2003) "The changing faces of glutathione, a cellular protagonist." (Translated from eng) Biochem Pharmacol, vol. 66(8): pp. 1499-1503 (in eng).
Setsukinai K, et al (2003) "Development of novel fluorescence probes that can reliably detect reactive oxygen species and distinguish specific species." (Translated from eng) J Biol Chem, vol. 278(5): pp. 3170-3175 (in eng).
Whiteman M & Halliwell B (1996) "Protection against peroxynitrite-dependent tyrosine nitration and alpha 1-antiproteinase inactivation by ascorbic acid. A comparison with other biological antioxidants." (Translated from eng) Free Radic Res, vol. 25(3): pp. 275-283 (in eng).
Radi R, et al, (2002) "Nitric oxide and peroxynitrite interactions with mitochondria." (Translated from eng) Biol Chem, vol. 383(3-4): pp. 401-409 (in eng).
Kumar A, et al, (2010) "Cell death mechanisms in the early stages of acute glutamate neurotoxicity." (Translated from eng) Neurosci Res, vol. 66(3): pp. 271-278 (in eng).
Radi R. et al, (2002) "Peroxynitrite reactions and formation in mitochondria," (Translated from eng) Free Radic Biol Med, vol. 33(11): pp. 1451-1464 (in eng).
Selkoe DJ (2004) "Cell biology of protein misfolding: the examples of Alzheimer's and Parkinson's diseases." (Translated from eng) Nat Cell Biol, vol. 6(11): pp. 1054-1061 (in eng).
Kubo T, et al, (2002) "In vivo conversion of racemized beta-amyloid([D-Ser26]A beta 1-40) to truncated and toxic fragments ([D-Ser 26]A beta 25-35/40) and fragment presence in the brains of Alzheimer's patients." (Translated from eng) J Neurosci Res, vol. 70(3): pp. 474-483 (in eng).
Esposito C, et al. (2006) "Exploring interaction of β-amyloid segment (25-35) with membrane models through paramagnetic probes." Journal of Peptide Science, vol. 12(12): pp. 766-774.
Millucci L, et al, (2009) "Rapid aggregation and assembly in aqueous solution of A beta (25-35) peptide." (Translated from eng) J Biosci, vol. 34(2): pp. 293-303 (in eng).
Cho DH, et al. (2009) "S-nitrosylation of Drp1 mediates beta-amyloid-related mitochondrial fission and neuronal injury." (Translated from eng) Science. vol. 324(5923): pp. 102-105 (in eng).
Glenner GG, et al (1984) "Alzheimer's disease: Initial report of the purification and characterization of a novel cerebrovascular amyloid protein." (Translated from eng) Biochem Biophys Res Commun, vol. 120(3): pp. 885-890 (in eng).
Sokolov, et al .,"Real-time vital optical imaging of precancer using anti-epidermal growth factor receptor antibodies conjugated to gold nanoparticles." Cancer Res. 2003, vol. 63:1999, 2004.
Niu, J., et al. "Cardiovascular effects of cerium oxide nanoparticles in a transgenic murine model of cardiomyopathy," Cardiovas. Res. Nov. 30, 2006, Nov. 2006, vol. 73, No. 3, pp. 549-559.
Qureshi, M.A., et al. "Increased exhaled nitric oxide following autologous peripheral hemotopietic stem cell transplantation; a potential marker of idopathic pneumonia syndrome," Chest, Jan. 2004, vol. 125, No. 1, pp. 281-287.
Ohgushi, et al., "Stem Cell Technology and Bioceramics: From Cell to Gene Engineering", J. Biomed. Mat. Res. 48: 913-927; 1999.
Dal Maschio, et al., "Influence of Ce3+/Ce 4+ ratio on phase stability and residual stress field in ceria-yttria stabilized zirconia plasma-sprayed coatings", J. Mat. Sci. 27: 5591-5596; 1992.
Ramsfjell, et al., "Distinct Requirements for Optimal Growth and In Vitro Expansion of Human CD341CD382 Bone Marrow Long-Term Culture-Initiating Cells (LTC-IC), Extended LTC-IC, and Murine In Vivo Long-Term Reconstituting Stem Cells", Blood 99: 4093-4102; 1999.
Devasenpathi, et al., "Forming near net shape free-standing components by plasma spraying", Mat. Let. 57: 882-886; 2002.
Imamura, et al. "Drusen, choridal neovascularization and retinal pigment epithelium dysfunction in SOD1-deficient mice: A model of age-related macular degeneration," PNAS, vol. 103, No. 30; 11282-11287 (Jul. 25, 2006).
Hollyfield, et al. "Oxidative damage-induced inflammation initiates age-related macular degeneration," Nature Medicine, vol. 14, pp. 194-198 (2008).
Birch, et al. Age-related macular degeneration: a target for nanotechnology derived medicines. International Journal of Nanomedicine, 2007, 2(1), 65-77.
Maulik, N. Reactive oxygen species drives myocardial angiogenesis? Antioxidants & Redox Signaling, 2006, 8 (11-12) 2161-2168.
Kuchibhatla et al., "Hierarchical assembly of inorganic nanostructure building blocks to octahedral superstructures a true template-free self-assembly", Nanotechnology, 2007, vol. 18, pp. 1-4.
Ohia, et al. "Pharmacological consequences of oxidative stress in ocular tissues," Mutation Research, 2005, 579, 22-36.
Liu, et al. "Subtype lesions of neovascular age-related macular degeneration in Chinese paitents," Braefe's Arch Clin Exp Opthalmol, 2007, 245, 1441-1445.
Silva. "Seeing the benefits of ceria," Nature Nanotechnology, 2006, 1, 92-94.
Hahn, et al. "Maculas affected by Age-Related Macular Degeneration Contain Increased Chelatable Iron in the Retinal Pigment Epithelium and Bruch's Membrane," Arch. Opthalmol. 2003, 121, 1099-1105.
Haywood, et al. "Inflammation and Angiogenesis in Osteoarthritis," Arthritis & Rheumatism, 2003, 48 (8), 2173-2177.
Chen, et al. Rare Earth Nanoparticles Prevent Retinal Degeneration Induced by Intracellular Peroxides: Nature Nano Technology, 1(2) 142-148 (2006).
Moongkarndi, et al. "Antiproliferation, antioxidation and induction of apoptosis by *Garcinia mangostana* (mangosteen) on SKBR3 human breast cancer cell line," J. of Ethno-Pharmacology, vol. 90, (2004) pp. 161-166.
Margrain, et al. "Do blue light filters confer protection against age-related macular degeneration?", Progress in Retinal and Eye Research, vol. 23 (2004) pp. 523-531.
Bailey, et al. "Cerium Oxide Nanoparticles Extend Cell Longevity and Act as Free Radical Scavengers," online (retrieved on Apr. 24, 2006) from: http://www.med.miami.edu/mnbws/Rzigalinski11.html.
Tsai, Ming-Shyong. "The Study of the synthesis of nano-grade cerium oxide powder," Materials Letters 58, 2270-2274 (2004).
Rzigalinski, Beverly Ann, et al. "Cerium Oxide nanoparticles increase the lifespan of cultured brain cells and protect against free radical mechanical trauma" FASEB Journal, vol. 17 No. 4-5, p.

(56) References Cited

OTHER PUBLICATIONS

Abstract No. 377.24 URL, XP008095016 & FASEB Meeting on Experimental Biology: Translating the Genome, San Diego, CA, USA, Apr. 11-15, 2003 ISSN: 0892-6638 Abstract.

Cook, et al. "Neuronal Damage induced by polychlorinated biphenyls is partically reversed by cerium oxide nanoparticles" [online] vol. 2003, 2003, XP008095032 Retrieved from the internet: URL http://sfn.scholarone.com/itin2003/main.htm]?new_page_id=126 &abstract_id=14513&p_num=669.13&is_tech=0> [retrieved on Aug. 5, 2008] abstract.

Tusnekawa, S., et al. "Lattice relaxation of monosize Ce02-x nanocrystalline particles" Applied Surface Science Elsevier Netherlands, vol. 152, No. 1-2, Nov. 1999, pp. 53-56.

Hooper, Claire, Y., et al. "New treatment in age-related macular degeneration" Clinical & Experimental Opthalmology, Oct. 2003, pp. 376-391.

Qi, et al. "Redispersible Hybrid Nanopowders; Cerium Oxide Nanoparticle complexes with Phosphonated-PEG Oligomers," ACS Nano, 2008, vol. 2(5), pp. 879-888.

Otsuka, et al. "PEGylated nanoparticles for biological and pharmaceutical applications," Advanced Drug Delivery Reviews, 2003, vol. 55, pp. 403-419.

Olivier, et al. "Synthesis of pegylated immunonanoparticles." Pharmaceutical Research, Aug. 2002, vol. 19, No. 8, pp. 1137-1143.

Shui, Y.B., et al. "Morphological observation on cell death an dphagocytosis induced by ultraviolet irradiation in a cultured human lens epithelial cell line," Dec. 2000, vol. 71, pp. 609-618.

Xijuan, et al. "Size-dependent optical properties of nanocrystalline Ce02:Er obtained by combustion synthesis," Sep. 24, 2001, Phys. Chem. Chem Phys., vol. 3, pp. 5266-5269.

Guo, "Green and red upconversion luminescence in Ce02:Er3+ powders produced by 785 nm laser," Jounral of Solid State Chemistry 180, p. 127-131, 2007.

Perez, J. M., et al. "Synthesis of Biocompatible Dextran-Coated Nanoceria with pH-Dependent Antioxidant Properties," Small, vol. 4 No. 5, 2008, pp. 552-556.

Pirmohamed, et al. "Nanoceria exhibit redox state-dependent catalase mimetic activity," Chem. Comm, 2010, 46, pp. 2736-2738.

Nazem, et al. "Nanotechnology for Alzheimer's disease detection and treatment." Insciences J., 2011, vol. 1(4), pp. 169-193.

Karakoti, et al. "Direct Synthesis of Nanoceria in Aqueous Polyhydroxyl Solutions." J. Phys. Chem. C, vol. 111, No. 46, 2007, pp. 17232-17240.

Tarnuzzer, et al. "Vacancy Engineered Ceria Nanostructures for Protection from Radiation-Induced Cellular Damage," Nano Lett, vol. 4, No. 12, pp. 2573-2577.

Heckert, et al. "The role of cerium redox state in the SOD mimetic activity of nanoceria," Biomaterials, 29, 2008, pp. 2705-2709.

Schubert, et al. "Cerium and yttrium oxide nanoparticles are neuroprotective," Feb. 2006, Biochemical and Biophysical Research Communications, 342, p. 86-91.

Zhang, et al. Cerium oxide nanoparticles: size selective formation and structure analysis, Jan. 2002, Applied Physics Letters, vol. 81, No. 1, p. 127-129.

Patil, et al. "Surface-derived nanoceria with human carbonic anhydrase II inhibitors and flourphores: a potential drug delivery device." J. Phys. Chem. C., 2007, vol. 111, No. 24, pp. 8437-8442.

Patil, et al. "Synthesis of nanocrystalline ceria particles for high temperature oxidation resistant coating," Journal of Nanoparticle Research, 2002, vol. 4: ppl. 433-438.

Jin, et al. "Nanopartical-mediated drug delivery and gene therapy," Biotechnol. Prog, 2007, vol. 23, pp. 32-41.

Eck, et al. "PEGylated gold nanoparticles conjugated to monoclonal F19 antibodies as targeted labeling agents for human pancreatic carcinoma tissue," ACS Nano, 2008, vol. 2(11) pp. 2263-2272.

Nafee. Dissertation entitled "Cationically-modified nanoparticles for the polmonary delivery of the telomerase inhibitor 2'-O-Methyl RNA for the treatment of lung cancer," Dissertation zur Erlangung des Grades des Doktors der, Naturwissenschaftern der Naturwissenschaftilch-Technischen Fakul't III Chemie, Pharmazie, Bio-und Werstoffwissenschaften der Universit des Saarlandes, 2008.

Suh et al., "Multifunctional nanosystems at the interface of physical and life sciences", Nano Today, 2009, vol. 4, pp. 27-36.

Suzuki et al., "Preparation and characteristics of magnetite labelled antibody with the use of poly(ethylene glycol) derivatives", Biotechnol. Appl. Biochem., 1995, vol. 21, pp. 335-345.

Monte et al., "Inhibition of lymphocyte induced angiogenesis by free radical scavengers", Free Radic Biol Med, 1994, vol. 17, pp. 259-266.

Buettner, et al., "Ascorbate (vitamin C, It's Antioxidant Chemistry", Presentation.

PCT/US2011/0044329; PCT International Search Report and Written Opinion.

* cited by examiner

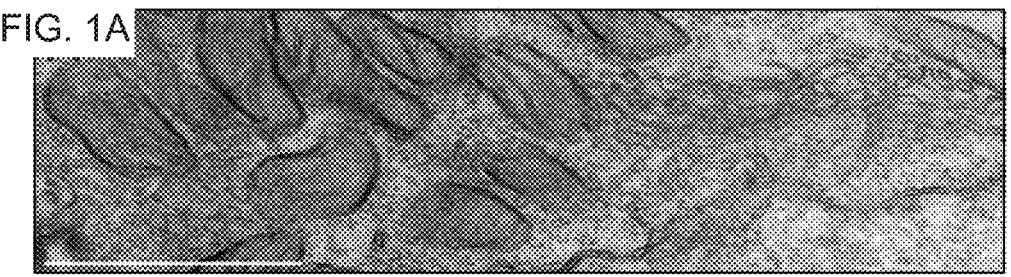
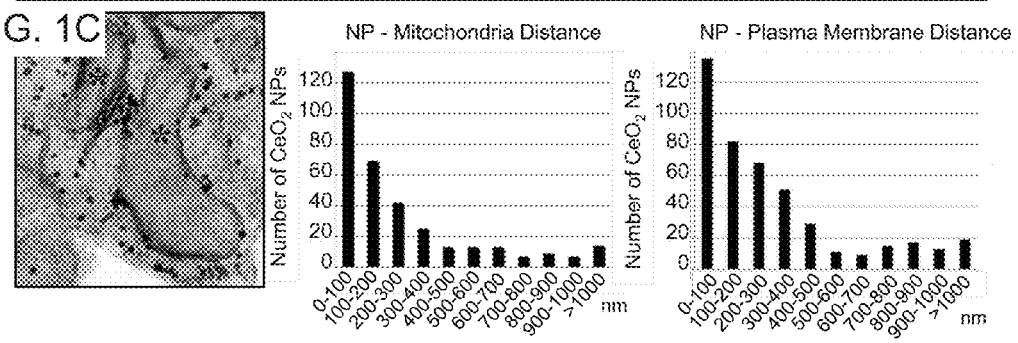
FIG. 1D  FIG. 1E

FIG. 4A
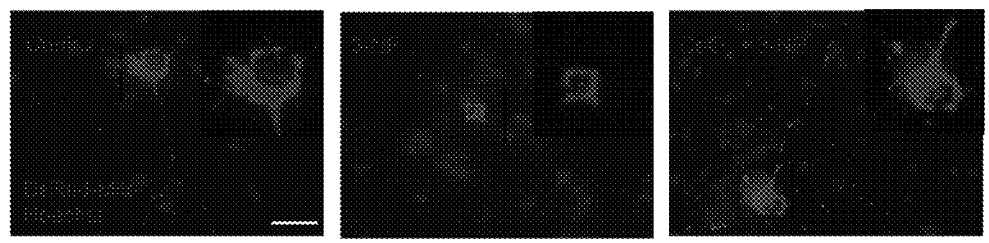
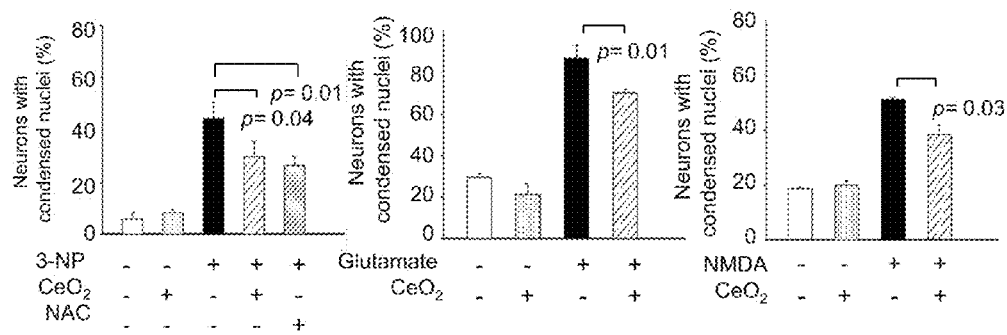
FIG. 4B                FIG. 4C                FIG. 4D FIG. 5A
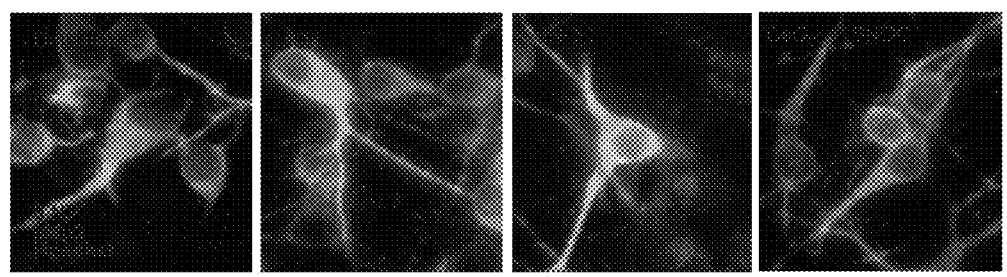
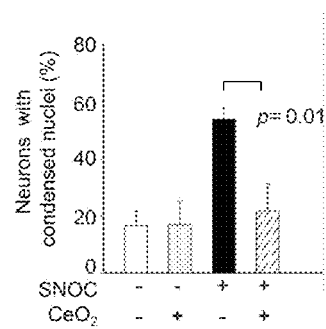
FIG. 5B
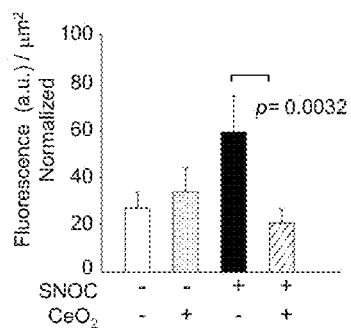
FIG. 5C
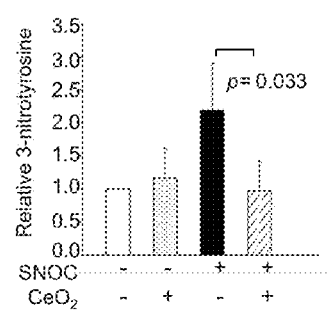
FIG. 5D

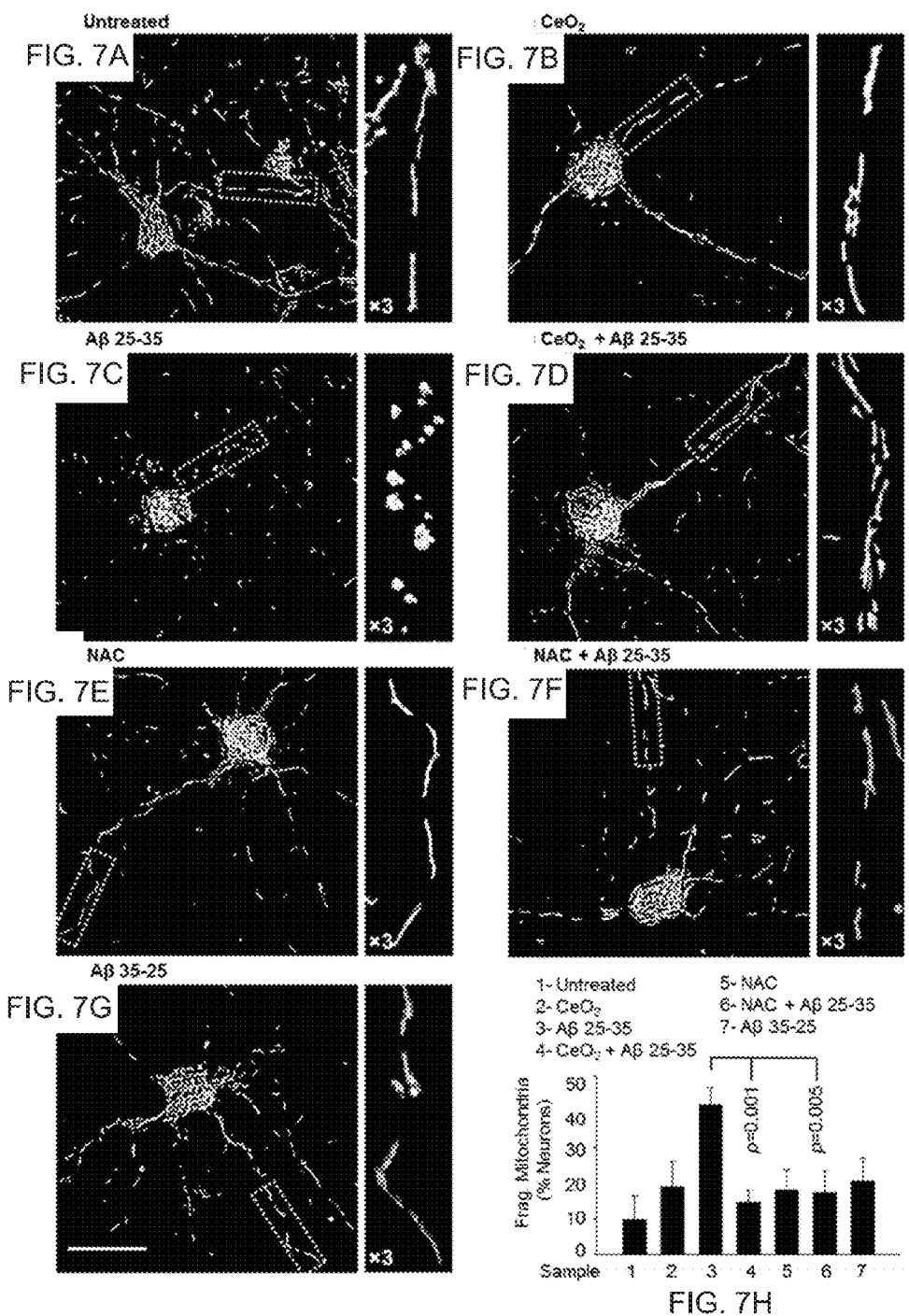

| Physico-Chemical Properties of $CeO_2$ NPs ||
|---|---|
| Size (nm) | 3-8 |
| Zeta Potential ($H_2O$) (mV) | 5.62 |
| Zeta Potential (buffer) (mV) | -16.26 |
| XPS peaks (eV) | 875-895, 895-910, 880.2, 899.5, 903.5 |
| EELS peaks (eV) | 883, 901 |

NEURONAL PROTECTION BY CERIUM OXIDE NANOPARTICLES

CROSS REFERENCE TO RELATED APPLICATIONS

The present application is a divisional of U.S. Ser. No. 13/624,485 filed Sep. 21, 2012 and further claims priority to U.S. Provisional Application Ser. No. 61/537,368 filed Sep. 21, 2011 under 35 USC 119, both of which are incorporated herein by reference.

FEDERAL FUNDING

This invention was made with Government support under agency contract/grant nos. R01 AG031529, R01 NS055193, R01 NS047456 and R01 EY016164 awarded by the National Institutes of Health and under CBET0708172 awarded by the National Science Foundation. The Government has certain rights in the this invention.

BACKGROUND

Neurodegeneration generally refers to the loss of structure or function of neurons, impairment of normal neuronal functions, and includes the death of neurons. Neurodegeneration results from various different causes including genetic mutation, mitochondrial dysfunction, and the inability to handle increasing levels of oxidative or nitrosative stress can also lead to the progression of neurodegeneration (67). Substantial evidence from many in vitro and in vivo studies suggests that there is a commonality of events for the progression of many neurodegenerative diseases of aging. Some of these neurodegenerative diseases include Parkinson's disease, Huntington's disease, Amyotrophic Lateral Sclerosis (ALS), and among the most common of the neurodegenerative disorders is Alzheimer's disease (AD). AD is a progressive and irreversible burden on patients, caregivers, and society (68). Mounting evidence in AD as well as in most neurodegenerative diseases shows an association with oxidative and nitrosative stress. Nitrosative stress and cell damage results when reactive nitrogen species (RNS) act together with reactive oxygen species (ROS).

Reactive oxygen species (ROS) and reactive nitrogen species (RNS) are formed during normal metabolism but an imbalance may result from the increase production of free radicals or from the failure of antioxidants and antioxidant enzymes to adequately scavenge the damaging molecules. This imbalance has been documented to be involved in AD (69). Several studies provide clear evidence that RNS, in particular peroxynitrite ($ONOO^-$) formation, contributes to the pathologies of chronic neurodegenerative diseases such as AD, Parkinson's disease, multiple sclerosis, and Amyotrophic lateral sclerosis (4). Peroxynitrite is formed from the reaction of nitric oxide radical (NO.) with superoxide ($O_2^{\cdot-}$). Mitochondrial injury seems to be a primary cause of $ONOO^-$ promoting neurotoxic effects (5, 6). Widespread $ONOO^-$ mediated damage is seen in brain tissue from AD in the form of increased protein nitration in neurons (7).

The administration of antioxidants and antioxidant enzymes to treat diseases due to increased ROS and RNS in human clinical trials have heretofore been less than satisfactory due to issues with bioavailability and stability after administration.

To answer this need, synthetic catalytic scavengers of ROS and RNS have been made and tested in various model systems. Copious metalloporphyrins have been synthesized to have high reactivity with, $O_2^{\cdot-}$, $H_2O_2$, NO. and $ONOO^-$ (14-17). Most studies affirm metalloporphyrins are useful tools for research and understanding the roles that ROS and RNS may play in diseases, however, their potential toxicity due to metals has often come into question for their use in humans.

Neurons have a high energy demand and contain several hundred mitochondria per cell and therefore have increased exposure to ROS and RNS. Mitochondria are a primary site of the intercellular formation of $ONOO^-$ (12) and mitochondrial dysfunction has been shown to contribute to disease or neuronal death (13). The ability to scavenge $ONOO^-$ is a critical therapeutic intercession in degenerative diseases associated the overproduction or unbalanced production of $O_2^{\cdot-}$ and NO and thus, $ONOO^-$.

To maintain their energy producing function, mitochondria must frequently divide and fuse. Evidence suggests that an imbalance in mitochondrial division and fusion plays a causal role in AD (78). Mitochondrial division and fusion is regulated by large GTPases of the dynamin family. Dynamin-related protein 1 (DRP1) is required for mitochondrial division. Inhibition of mitochondrial division by expression of the GTPase defective DRP1$^{K38A}$ mutant provides protection against excessive NO, NMDA, or Aβ (5). The exact mechanism that accounts for the NO-induced mitochondrial fragmentation remains unclear. A recent report suggested that S-nitrosylation of DRP1 at cysteine 644 increases DRP1 activity and is the cause for the peroxynitrite-induced mitochondrial fragmentation in AD (85, 50). However, the work remains controversial, suggesting alternative pathways might be implicated (85, 86). Nitrosative stress causes rapid DRP1 Serine 616 (S616) phosphorylation, which promotes its translocation to mitochondria and organelle division (86, 87). In mitotic cells DRP1 S616 phosphorylation is mediated by Cdk1/cyclinB1 and synchronizes mitochondrial division with cell division (88, 89). Interestingly, p-DRP1 S616 levels are markedly increased in brains of individuals with AD, suggesting that this event might contribute to the change in mitochondrial morphology and energy metabolism in AD (86, 88). The kinase responsible for DRP1 S616 hyperphosphorylation in AD is unknown, but Cdk5/p25 is a potential candidate kinase mediating this process (7, 90). Notably, aberrant Cdk5/p25 signaling causes tau hyperphosphorylation in postmitotic neurons and is implicated in Aβ-mediated neurodegeneration (88, 91-93).

SUMMARY

The effects that Alzheimer disease and other neurodegenerative diseases have on the brain include physical changes in the brain. Some of those changes include the development of characteristic plaques and neurofibrillary tangles. The activation of microglia in response to injury, illness, aging or other causes initiates events that are characterized as an inflammatory process. These events are first mediated by the proinflammatory cytokine interleukin 1, which is overexpressed by the activated microglia. Through various pathways, interleukin 1 causes neuronal death, which activates more microglia, which in turn releases more interleukin 1 in a self-sustaining and self-amplifying fashion. Over time, this slow, smoldering inflammation in the brain destroys sufficient neurons to cause the clinical signs of Alzheimer disease.

Cerium oxide nanoparticles ($CeO_2$ NPs) have recently been shown to effectively scavenge reactive oxygen species in a variety of model systems. The mechanism by which cerium oxide nanoparticles catalyze these redox reactions relate to the surface chemistry and redox state of cerium and is preparation dependent. Peroxynitrite, a highly neurotoxic reactive nitrogen species is functionally implicated in the pathogenesis of a broad spectrum of neurodegenerative disorders. Scavenging peroxynitrite provides beneficial therapeutic effects in both neurodegenerative diseases and in many diseases where inflammation in the brain is a critical contributing factor. Conventional antioxidants primarily scavenge only reactive oxygen species, and are ineffective against reactive nitrogen species. It has been discovered that cerium oxide, a rare earth oxide nanomaterial, scavenges peroxynitrite in vitro. This newly discovered catalytic property of cerium oxide provides protection in a primary neuronal cell model. Cerium oxide nanoparticles are internalized by neurons and accumulate around mitochondria, the primary source of reactive nitrogen species in neurons. Cerium oxide nanoparticles convey neuroprotection against exogenous nitric oxide or endogenous peroxynitrite mediated by mitochondrial toxins, excess glutamate or Aβeta peptide. Neuroprotection by these rare earth nanoparticles is accompanied by lower protein tyrosine nitration and reduction of reactive nitrogen species. Given the critical role that peroxynitrite plays in neurodegenerative diseases, a novel discovery that cerium oxide nanoparticles present a new therapeutic approach to lowering peroxynitrite levels and preventing neurodegeneration has been made.

Cerium oxide nanoparticles have low toxicity (18, 19). It has been discovered that the ability to switch between the $3^+$ and $4^+$ oxidation states gives $CeO_2$ NPs a unique antioxidant function.

$CeO_2$ NPs have been shown to protect several cell types and animal models against ROS mediated diseases (20). Nanoparticles in general exhibit novel surface properties that can affect their chemistry and their interaction with biological systems. $CeO_2$ NPs are comprised of a crystalline lattice and due to their nanometer length scale, oxygen defects at the surface are present that yield reactive sites. Within these sites, $CeO_2$ NPs have the ability to interchange between the $3^+$ and $4^+$ oxidation state (21). The relative level of vacancies and thus reactive sites is difficult to control, however success has been achieved herein in generating $CeO_2$ NPs with varied ratios of Ce in the $3^+/4^+$ state. $CeO_2$ NPs with higher $3^+/4^+$ ratio are superoxide dismutase (SOD) mimetics and exhibit efficient SOD activity (21, 22) when compared to $CeO_2$ NPs with lower $3^+/4^+$ ratio. It should be noted that $CeO_2$ NPs with lower $3^+/4^+$ ratio exhibit increased catalase mimetic activity (23). Indeed, $CeO_2$ NPs have been shown to be neuroprotective in various neuronal culture models (24-26). Recent in vivo studies affirm the antioxidant effects of $CeO_2$ NPs with low toxicity to the brain in rodent models (27, 28). The ability of $CeO_2$ NPs to react with $ONOO^-$ in vitro and an assessment of the neuroprotective properties of $CeO_2$ NPs during nitrosative stress is provided herein. Also provided herein is a demonstration that certain $CeO_2$ NPs protect against Aβ-induced DRP1 S616 hyperphosphorylation, mitochondrial fragmentation and neuronal cell death

BRIEF DESCRIPTION OF THE DRAWINGS

FIG. 1A is a transmission electron microscopy (TEM) showing a control culture.

FIG. 1B is a TEM showing $CeO_2$ NPs within the neurons, associated with mitochondria and plasma membranes.

FIG. 1C is a TEM showing $CeO_2$ NPs within the neurons, associated with mitochondria and plasma membranes.

FIG. 1D is a chart showing the quantification of $CeO_2$ NPs associated with mitochondria.

FIG. 1E is a chart showing the quantification of $CeO_2$ NPs associated with plasma membrane.

FIG. 4A shows the protective effects of pre-treatment with $CeO_2$ NPs on cortical neurons in the right panel, the left panel provides a control view, and the center panel provides a view showing cell death.

FIG. 4B shows a comparison between $CeO_2$ NPs and NAC (N-acetyl-L-cysteine), the effect of $CeO_2$ NPs on neurons challenged with glutamate, and the effect of $CeO_2$ NPs on cell death caused by overstimulation of NMDA receptors.

FIG. 4C shows that $CeO_2$ NPs were neuroprotective after neurons were challenged with glutamate.

FIG. 4D shows that death caused by overstimulation of NMDA receptors with NMDA was overcome when $CeO_2$ NPs were present.

FIGS. 5A-D shows the effect of $CeO_2$ NPs on 3-nitrotyrosine modification in an in vitro cell culture. FIG. 5A represents images showing an increase in 3-NT signal in SNOC treated cortical neurons. FIG. 5B: cultures were scored for cell death and it was observed that treatment with $CeO_2$ NPs rescued the SNOC treated cultures from cell death. FIG. 5C shows a decrease in the 3-NT signal in cultures pretreated with $CeO_2$ NPs was detected. FIG. 5D pretreatment with $CeO_2$ NPs abrogated the 3-NT formation, as measured by densitometry.

FIGS. 7A-7H Nanoceria prevent Aβ-induced mitochondrial fragmentation. FIG. 7A shows fluorescence micrograph (scale bar, 50 µm) and 3× zoom of boxed regions of mitochondrial morphology in neurons expressing DsRed2-Mito left untreated. FIG. 7B shows fluorescence micrograph (scale bar, 50 µm) and 3× zoom of boxed regions of mitochondrial morphology in neurons expressing DsRed2-Mito treated with nanoceria (100 nM) (3 h pretreatment), FIG. 7C shows fluorescence micrograph (scale bar, 50 µm) and 3× zoom of boxed regions of mitochondrial morphology in neurons expressing DsRed2-Mito treated with Aβ 25-35 (10 µM), FIG. 7D shows fluorescence micrograph (scale bar, 50 µm) and 3× zoom of boxed regions of mitochondrial morphology in neurons expressing DsRed2-Mito treated with nanoceria and Aβ 25-35, FIG. 7E shows fluorescence micrograph (scale bar, 50 µm) and 3× zoom of boxed regions of mitochondrial morphology in neurons expressing DsRed2-Mito treated with NAC (50 µM) (3 h pretreatment), FIG. 7F shows fluorescence micrograph (scale bar, 50 µm) and 3× zoom of boxed regions of mitochondrial morphology in neurons expressing DsRed2-Mito treated with NAC and Aβ 25-35, FIG. 7G shows fluorescence micrograph (scale bar, 50 μm) and 3× zoom of boxed regions of mitochondrial morphology in neurons expressing DsRed2-Mito treated with the reverse Aβ 35-25 (10 μM) peptide for six hours. FIG. 7H is a graph pertaining to mitochondrial fragmentation in neurons expressing DsRed2-Mito and after treatment for six hours with nanoceria, NAC, or Aβ 25-35 alone or in combination with either nanoceria and Aβ 25-35 or NAC and Aβ 25-35. Data are representative of three or more independent experiments. Results are means±s.d. Statistics: Student's t test.

FIG. 8A shows western blots of p-DRP1 S616, total DRP1, and actin protein levels from neurons exposed for three hours to aged SNOC (100 μM), nanoceria (100 nM) (3 h pretreatment), or fresh SNOC (100 μM) alone or in combination. The bar graph represents the relative ratios of p-Drp1 S616 to total DRP1 protein and normalized to actin. FIG. 8B shows western blots of p-DRP1 S616, total DRP1, and actin protein levels from neurons exposed to nanoceria (100 nM), preaggregated 10 μM Aβ 25-35 for 6 h, or in combination as well as NAC (50 μM) (3 h pretreatment) with Aβ 25-35. The bar graph illustrates the relative ratios of p-DRP1 S616 to total DRP1 protein, normalized to actin.

FIG. 9A is a graph showing cell death of neurons treated with either nanoceria (100 nM) (3 h pretreatment), NAC (50 μM) (3 h pretreatment), or Aβ 25-35 (10 μM) alone, or both nanoceria and Aβ 25-35, or NAC and Aβ 25-35 at six hours. Untreated cells or reverse Aβ 35-25 (10 μM) peptide treatment served as negative controls. FIG. 9B is a graph showing excitotoxic cell death of neurons exposed to either NMDA (150 μM), or nanoceria (100 nM) (3 h pretreatment), or in combination of both for 12 hours. FIG. 9C is a graph showing excitotoxic cell death of neurons exposed to either glutamate (150 μM), or nanoceria (100 nM) (3 h pretreatment), or in combination of both for six hours. FIG. 9D is a graph showing cell death of neurons exposed to mitochondrial respiratory complex II inhibitor 3-NP (10 mM), or nanoceria (100 nM) (3 h pretreatment), or in combination of both for eight hours. Results are representative of three or more independent experiments. Data are means±s.d. Statistics: Student's t test.

FIGS. 10A-10D Physico-Chemical Properties of Cerium Oxide Nanoparticles ($CeO_2$ NPs). FIG. 10A pertains to a table listing the properties of the $CeO_2$ NPs used in this study are typical and indicative of $CeO_2$ NPs in the $3^+$ state. FIG. 10B pertains to energy-dispersive X-ray (EDX) analysis of $CeO_2$ NPs supports presence of both cerium and oxygen. FIG. 10C pertains to a selected area (electron) diffraction (SAED) pattern of $CeO_2$ NPs corresponds to fluorite pattern for ceria. FIG. 10D pertains to a UV-Vis graph of sterile filtered $CeO_2$ NPs used in tissue culture experiments confirming $3^+$ oxidation state of $CeO_2$ NPs. Absorbance between 230-260 nm is indicative of $3^+$ oxidation state.

FIG. 12A shows a graph of peroxynitrite absorbance followed at 302 nm in 100 mM sodium phosphate buffer at pH 8.6. (N=4). GSH, known general scavenger and $SiO_2$ NPs were added as positive and negative controls, respectively. Rate of $ONOO^-$ (black traces) decomposition was increased with $CeO_2$ NPs (blue traces) in a similar manner of GSH (red traces). Rate of decomposition was not affected by presence of $SiO_2$ NPs (green traces). FIG. 12B shows a graph of 100 mM sodium phosphate buffer at pH 9.5. (N=3). Rate of $ONOO^-$ (black traces) decomposition was increased with $CeO_2$ NPs (blue traces) in a similar manner of GSH (red traces). Absorbance was normalized by subtracting the final absorbance from initial absorbance and dividing by the amplitude. As stock solutions of $ONOO^-$ contain 0.3 M NaOH, control incubations were performed with equivalent amounts of NaOH. All in vitro experiments were performed using phosphate buffers containing 1 μM DPTA.

DETAILED DESCRIPTION

Figures 2A, 2B:
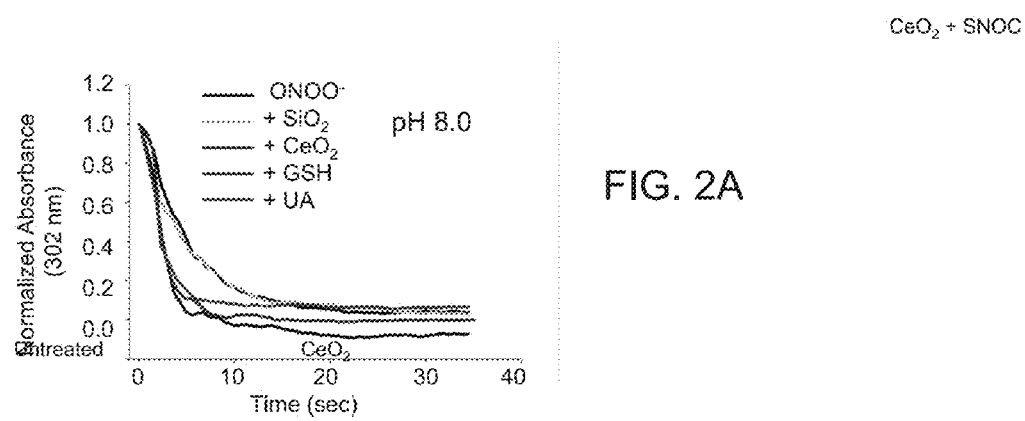
FIG. 2A shows graph views of a UV visible spectroscopy used to examine the strong absorbance peroxynitrite exhibits at 302 nm and its decay. The decay of $ONOO^-$ was followed in the absence and presence of $CeO_2$ NPs.
FIG. 2B provides a graphical representation of $ONOO^-$ scavenging abilities of $CeO_2$ NPs, viewable by following the yield of oxidized APF by fluorescent spectroscopy using the oxidizable probe, 3'-(p-aminophenyl) fluorescein (APF) as an indicator.

The specifics of the discovery include the use of cerium oxide nanoparticles that specifically decrease peroxynitrite levels in a subject to treat specific conditions such as Alzheimer's disease and other neurodegenerative diseases as outlined below.

In one embodiment, a method of treating a subject with elevated levels of peroxynitrite, is provided, the method includes administering a therapeutically effective amount of cerium oxide nanoparticles to the subject, wherein the cerium oxide nanoparticles reduce the level of peroxynitrite in the subject. In a particular embodiment, the cerium oxide nanoparticles range between 1-5 nanometers in size. In another embodiment, the cerium oxide nanoparticles range between 5-10 nanometers in size. In another embodiment, the method is provided wherein the cerium oxide nanoparticles scavenge peroxynitrite.

In yet another embodiment, a method of treating a subject identified as at risk of developing a neurodegenerative disease is provided. The method includes administering a therapeutically effective amount of cerium oxide nanoparticles (CeO2NPs) to the subject, wherein the cerium oxide nanoparticles scavenge reactive oxygen species (ROS) and reactive nitrogen species (RNS) in the subject. In a specific embodiment, the method is provided wherein the RNS is peroxynitrite.

In another embodiment, the cerium oxide nanoparticles used and which are effective to scavenge peroxynitrite have a higher ratio of 3+ to 4+ state. Reference to cerium oxide nanoparticles having a higher 3+/4+ ratio means that the percentage of cerium in the 3+ state is greater than the percentage of cerium in the 4+ state. In a more specific embodiment, a higher 3+/4+ ratio means that the percentage of cerium in the 3+ state is greater than 50 percent.

Neurodegenerative diseases include but are not limited to Alzheimer's disease, Parkinson's disease, Amyotrophic lateral sclerosis, Friedreich's ataxia, Huntington's disease, or Lewy body disease. A subject at risk of developing a neurodegenerative disease can be identified by detecting or observing a number of different signs and symptoms in the subject. Some of those signs and symptoms include amyloid plaques in the brain, and/or neurofibrillary tangles (NFTs) in the brain.

In the case of Alzheimer's disease, eight cognitive domains are most commonly impaired, including memory, language, perceptual skills, attention, constructive abilities, orientation, problem solving and functional abilities (70).

Also, a decrease in activity in the temporal lobe is observed in AD development, such as through the use of known imaging techniques such as PET scan or MRI. Thus, according to one embodiment, a patient at risk would be an individual who has impairment in cognition and/or decreased activity in the temporal lobe. When available as a diagnostic tool, single photon emission computed tomography (SPECT) and positron emission tomography (PET) neuroimaging are used to confirm a diagnosis of Alzheimer's in conjunction with evaluations involving mental status examination (71). In a person already having dementia, SPECT appears to be superior in differentiating Alzheimer's disease from other possible causes, compared with the usual attempts employing mental testing and medical history analysis (72).

A new technique known as PiB PET has been developed for directly and clearly imaging beta-amyloid deposits in vivo using a tracer that binds selectively to the A-beta deposits. The PiB-PET compound uses carbon-11 PET scanning. Recent studies suggest that PiB-PET is 86% accurate in predicting which people with mild cognitive impairment will develop Alzheimer's disease within two years, and 92% accurate in ruling out the likelihood of developing Alzheimer's. A similar PET scanning radiopharmaceutical compound called (E)-4-(2-(6-(2-(2-(2-([$^{18}$F]-fluoroethoxy)ethoxy)ethoxy)pyridin-3-yl)vinyl)-N-methyl benzenamine, or $^{18}$F AV-45, or florbetapir-fluorine-18, or simply florbetapir, contains the longer-lasting radionuclide fluorine-18, has recently been created, and tested as a possible diagnostic tool in Alzheimer's patients. Florbetapir, like PiB, binds to beta-amyloid, but due to its use of fluorine-18 has a half-life of 110 minutes, in contrast to PiB's radioactive half life of 20 minutes. Wong et al. found that the longer life allowed the tracer to accumulate significantly more in the brains of the AD patients, particularly in the regions known to be associated with beta-amyloid deposits. Thus, in specific embodiment, a patient at risk is one that has increased a-beta deposits.

Volumetric MRI can detect changes in the size of brain regions. Measuring those regions that atrophy during the progress of Alzheimer's disease is showing promise as a diagnostic indicator. Thus, according to another specific embodiment, an at-risk patient is one that has an atrophic brain region.

Another recent objective marker of the disease is the analysis of cerebrospinal fluid for amyloid beta or tau proteins, both total tau protein and phosphorylated tau$_{181P}$ protein concentrations. Searching for these proteins using a spinal tap can predict the onset of Alzheimer's with a sensitivity of between 94% and 100%. Thus, according to another specific embodiment, a patient at risk is one that has elevated levels of tau and/or amyloid beta proteins in cerebral spinal fluid. When used in conjunction with existing neuroimaging, doctors can identify patients with significant memory loss who are already developing the disease (73). Spinal fluid tests are commercially available, unlike the latest neuroimaging technology. Alzheimer's was diagnosed in one-third of the people who did not have any symptoms in a 2010 study, meaning that disease progression occurs well before symptoms occur. Changes in brain ventricle size may be measured by magnetic resonance imaging (MRI). This measurement provides, in another embodiment, the ability to diagnose pre-Alzheimer's disease or early stages of the disease in some cases. While neuro-cognitive assessments including the testing of memory, ability to problem solve, count, and other cognitive tests provides a diagnosis for Alzheimer's disease, a definitive diagnosis is not possible in the prior art until after death when an autopsy can be used to reveal the presence of amyloid plaques and tangles in brain tissue. Improvements have been made such that an earlier diagnosis may be made by identifying an increase in ventricle size in the brain associated with mild cognitive impairment in patients at risk for Alzheimer's disease or in the early stages of the disease. Therefore, according to a specific embodiment, a patient is at risk for a neurodegenerative disease, particularly AD, if the patient exhibits one or more of the foregoing factors or symptoms. In another specific embodiment, a patient at risk exhibits two or more of the aforementioned factors or symptoms.

In the case of Parkinson's disease (PD), a pattern of reduced dopaminergic activity in the basal ganglia can aid in diagnosis. Thus, in another specific embodiment, a patient at risk is one that has reduced dopaminergic activity in the basal ganglia. Also, Parkinson's disease affects movement, producing motor symptoms, such as Parkinsonian gait, tremors, rigidity, slowness of movement and postural instability. Non-motor symptoms, which include autonomic dysfunction, neuropsychiatric problems (mood, cognition, behavior or thought alterations), and sensory and sleep difficulties, are also common. Thus, according to another specific embodiment, a patient at risk is one that exhibits one or more motor or non-motor PD symptoms. In an even more specific embodiment, a patient at risk is one that has two or more of the foregoing factors or symptoms.

In a further embodiment, a method of reducing brain inflammation in a patient is provided. The method includes administering a therapeutically effective amount of cerium oxide nanoparticles to the patient, the cerium oxide nanoparticles effective to reduce peroxynitrite levels in the brain.

In still a further embodiment, a method of scavenging reactive nitrogen species in a subject is provided. The method includes administering a therapeutically effective amount of cerium oxide nanoparticles to the subject, wherein the cerium oxide nanoparticles associate with a membrane in the subject and accelerate decomposition of the reactive nitrogen species in the subject. The method is provided wherein the reactive nitrogen species is peroxynitrite. In a more specific embodiment, the membrane is a mitochondrial membrane and/or a plasma membrane.

The following examples are provided as an aid in examining particular aspects of the invention, and represent only certain embodiments and explanations of embodiments. The examples are in no way meant to be limiting of the invention scope. The materials and methods provided below are those which were used in performing the examples that follow.

EXAMPLES

Example 1: Cerium Oxide Nanoparticles are Taken Up and Localize to the Periphery of Mitochondria and the Inner Surface of the Plasma Membrane in Primary Cortical Neurons Uptake of nanomaterials by cells has been shown to vary depending upon nanoparticle size, shape, composition, as well as surface modifications. In addition, diverse cell types control differentially the uptake and translocation of nanoparticles (33). Understanding cellular responses to nanoparticles are vital to their becoming therapeutic, therefore the way in which cells internalize and traffic the CeO$_2$ NPs was a critical discovery.

Pure cortical neuronal cultures were treated with 100 nM CeO$_2$ NPs for 3, 12 and 24 h and processed for transmission electron microscopy (TEM). Compared to control cultures (FIG. 1A), CeO$_2$ NPs were found within the neurons, however, CeO$_2$ NPs were not found in the nuclei of the neurons (FIG. 1B). CeO$_2$ NPs were identified in two primary locations, one associated with mitochondria and a second along the plasma membranes (FIGS. 1B&C). Quantification of CeO$_2$ NPs association with mitochondria (FIG. 1D) or plasma membrane (FIG. 1E) show their location aligns with the primary sources of reactive nitrogen species in neurons. The physico-chemical properties of $CeO_2$ NPs were determined using parallel samples to confirm the $3^+$ oxidation state, fluorite structure and cerium spectrum (Supplementary FIG. 1A-D Physico-Chemical Properties of Cerium Oxide Nanoparticles (CeO2 NPs). A. Table listing the properties of the CeO2 NPs used in this study are typical and indicative of CeO2 NPs in the 3+ state. B. Energy-dispersive X-ray (EDX) analysis of CeO2 NPs supports presence of both cerium and oxygen. C. Selected area (electron) diffraction (SAED) pattern of CeO2 NPs corresponds to fluorite pattern for ceria. D. UV-Vis graph of sterile filtered CeO2 NPs used in tissue culture experiments confirming 3+ oxidation state of CeO2 NPs. Absorbance between 230-260 nm is indicative of Ce 3+ oxidation state.). The size of the $CeO_2$ NPs averaged between 3-8 nm with zeta potentials measuring 5.62 eV for nanoparticles added to the neuronal cultures and zeta potentials measuring −16.26 mV in phosphate buffer in the in vitro assays, as previously reported (34). It is characteristic for oxide nanoparticles to rapidly agglomerate in biological fluids (35) due to a correlation between surface charge and opsonization (36) along with their sensitivity to local environments. To confirm that the electron dense granules seen in cells originated from the CeO2 NPs treatment, non-post-stained images (Supplementary FIG. 2 CeO2 NPs in cortical neurons. TEM section without post-stain assures that the dense particles are from addition of CeO2 NPs and not due to staining artifact) showed the same agglomerated, 15-25 nm dense particles as the post-stained images. High resolution (HR)-TEM of the water-based $CeO_2$ NPs used in the TEM experiments show the characteristic (111) ceria surface (FIG. 1B inset). $CeO_2$ NPs were identified in cortical cultures, especially located in close proximity to membranes.

Example 2: Effect of $CeO_2$ NPs on the Rate of Decay of $ONOO^-$ In Vitro

Peroxynitrite's involvement in many diseases makes it a concern that must be addressed (4). The half-life of $ONOO^-$ is on the order of seconds at physiological pH but that is enough time for it to diffuse a long distance to a target site. To initiate the potential use of $CeO_2$ NPs for therapeutic use, the effect that $CeO_2NP$ had on the decomposition of $ONOO^-$ was tested.

Peroxynitrite exhibits a strong absorbance at 302 nm and its decay can thus be followed using UV-visible spectroscopy (37). The decay of $ONOO^-$ was followed in the absence and presence of $CeO_2$ NPs (FIG. 2A and Supplementary FIG. 3: Effect of CeO2 NPs on the rate of decay of ONOO— in vitro varying pH. ONOO— (25 µM) was added at various pH's alone and in the presence of CeO2 NPs (100 µM), SiO2 NPs (100 µM), glutathione (GSH) (0.5 mM). (A) Peroxynitrite absorbance followed at 302 nm in 100 mM sodium phosphate buffer at pH 8.6. (N=4). GSH, known general scavenger and SiO2 NPs were added as positive and negative controls, respectively. Rate of ONOO—(black traces) decomposition was increased with CeO2 NPs (blue traces) in a similar manner of GSH (red traces). Rate of decomposition was not affected by presence of SiO2 NPs (green traces). B) 100 mM sodium phosphate buffer at pH 9.5. (N=3). Rate of ONOO—(black traces) decomposition was increased with CeO2 NPs (blue traces) in a similar manner of GSH (red traces). Absorbance was normalized by subtracting the final absorbance from initial absorbance and dividing by the amplitude. As stock solutions of ONOO— contain 0.3 M NaOH, control incubations were performed with equivalent amounts of NaOH. All in vitro experiments were performed using phosphate buffers containing 1 µM DPTA.). The in vitro assays were repeated using various phosphate buffers while varying the pH's. Since carbon dioxide is known to enhance the rate of $ONOO^-$ decomposition (38), the change in absorbance at 302 nm was followed in potassium phosphate buffer (pH 8.0), which was degassed by argon. The rate of $ONOO^-$ decomposition was increased by the addition of $CeO_2$ NPs in a manner comparable to uric acid, a known scavenger of $ONOO^-$ (FIG. 2A). Similarly, the rate of $ONOO^-$ decomposition was increased in the presence of $CeO_2$ NPs in sodium phosphate buffer at both pH 8.6 and 9.5 (Supplementary FIGS. 3 A&B). This change of absorbance in response to addition of $CeO_2$ NPs in these studies also mimics the scavenging seen with glutathione, a known antioxidant that protects cells from free radicals and peroxides (39). To confirm specificity, an unrelated oxide NP was tested, (silicon oxide ($SiO_2$) NPs) to determine if this potential scavenger behavior was unique to $CeO_2$ NPs. $SiO_2$ NPs did not accelerate the decay of $ONOO^-$. Addition of $ONOO^-$ after two minutes again resulted in faster decomposition of $ONOO^-$ in the presence of $CeO_2$ NPs, showing that these reactions are catalytic and the catalyst is not degraded significantly during the reaction. In every case the rate of decomposition of $ONOO^-$ in the presence of $CeO_2$ NPs was faster reflecting a reaction between $ONOO^-$ and the $CeO_2$ NPs.

Example 3: $CeO_2$ NPs Interact with $ONOO^-$ In Vitro and Prevent APF Oxidation To obtain further insight into the $ONOO^-$ scavenging abilities of $CeO_2$ NPs, the yield of oxidized APF was followed by fluorescent spectroscopy using the oxidizable probe, 3'-(p-aminophenyl) fluorescein (APF) as an indicator (FIG. 2B). APF is an aromatic amino-fluorescein derivative that has little intrinsic fluorescence but undergoes oxidation by only hydroxyl radical, hypochlorate ion, and certain peroxidase intermediates such as $ONOO^-$, but is inert to NO., $O_2^{.-}$ and $H_2O_2$ (40). $CeO_2$ NPs prevented the oxidation of APF in a manner that was similar to glutathione and uric acid, known scavengers of $ONOO^-$ (41). Again, an unrelated oxide NP was tested ($SiO_2$ NPs) which did not scavenge $ONOO^-$ and thus did not prevent the oxidation of APF. Thus evidence has been found that $CeO_2$ NPs can facilitate $ONOO^-$ decomposition using two, independent methods to measure $ONOO^-$.

Example 4: $CeO_2$ NPs Reduce $ONOO^-$ in Cortical Neuronal Cultures

Figure 3A:
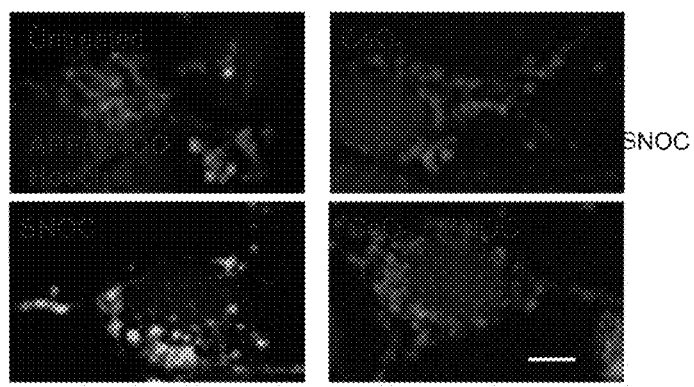
FIG. 3A provides a comparison of the effects on cortical neuronal cultures of $CeO_2$, SNOC, and $CeO_2$+SNOC.
Figure 3B:
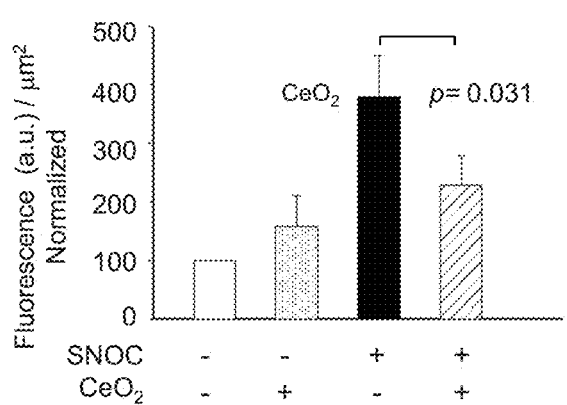
FIG. 3B shows a further quantitative analysis using fluorescence, determined by total pixel per intensity per $\mu m^2$.

RNS, in particular $ONOO^-$ formation, contributes to the pathologies of chronic neurodegeneration including AD (7). To test this hypothesis, the in situ $ONOO^-$ formation in live cells was followed again using the oxidizable probe, APF as an indicator. Exogenous NO. was added to mixed cortical neuronal cultures using the NO. donor S-nitrosocysteine (SNOC). Neurons treated with SNOC causes NO./$ONOO^-$ inhibition of the respiratory chain complexes (42) leading to alterations in mitochondrial function. In FIG. 3A, the lower left panel contains a representative image of cortical neuronal cultures when challenged with SNOC. The presence of $ONOO^-$ is denoted by an increase of fluorescence. When dosed with $CeO_2$ NPs, the fluorescence is decreased (FIG. 3A lower right panel). Further quantitative analyses using fluorescence was determined by total pixel intensity per $\mu m^2$ (FIG. 3B). Cells exposed to $CeO_2$ NPs before SNOC addition had appreciably reduced fluorescence compared to cells treated with SNOC alone reflecting a lower level of $ONOO^-$.

Example 5: Cortical Neuronal Cultures are Protected from Nitrosative Stress by Pretreatment with $CeO_2$ NPs It was tested whether $CeO_2$ NPs would rescue neurons from a variety of stressors that would increase an imbalance between RNS and endogenous antioxidants. To assess the neuronal protection capabilities of $CeO_2$ NPs, pure cortical neuronal cultures transfected with DsRed2-Mito were pretreated with $CeO_2$ NPs (100 nM) and subjected to various treatments known to increase RNS. Representative images show control neuronal cells with elongated mitochondria with normal euchromatin in the soma of the neurons (FIG. 4A left panel). Cell death was evaluated by condensed nuclei accompanied by shrunken soma and mitochondrial fragmentation (FIG. 4A center panel). Pretreatment of neurons with $CeO_2$ NPs rescued neurons as visualized by return of soma to normal size, nuclei were no longer condensed and mitochondria were again elongated (FIG. 4A right panel). 3-Nitropropionic acid (3-NP) is an irreversible inhibitor of complex II and is toxic to neurons via an N-methyl-D-aspartate (NMDA) and reactive oxygen species (ROS) dependent pathway (30).

$CeO_2$ NPs were able to prevent neuronal cell death by 3-NP. These results modeled N-acetyl-L-cysteine (NAC), a well characterized cell culture antioxidant which is rapidly metabolized to intracellular glutathione (FIG. 4B). Early stages of acute glutamate induced neurotoxicity includes elevated $ONOO^-$ production (43), (44). Again, $CeO_2$ NPs were neuroprotective after neurons were challenged with glutamate (FIG. 4C). Additionally, death caused by overstimulation of NMDA receptors with NMDA was overcome when $CeO_2$ NPs were present (FIG. 4D). These results suggest that in the presence of $CeO_2$ NPs, reactive $ONOO^-$ is removed and cortical neurons are rescued from cell death caused by nitrosative stress.

Example 6: $CeO_2$ NPs Reduce 3-Nitrotyrosine Modification in In Vitro Cell Culture Neurons have a high energy demand and contain several hundred mitochondria per cell and therefore have increased exposure to reactive oxygen species (ROS) and RNS (13). Mitochondria are also a primary site of the intercellular formation of $ONOO^-$ (45). To understand the mechanism of neuronal protection seen by $CeO_2$ NPs, $ONOO^-$ and its ability to promote the nitration of tyrosine residues was considered. To substantiate that $CeO_2$ NPs can scavenge $ONOO^-$ and prevent the post-translational modification 3-nitrotyrosine, exogenous NO. was added to mixed cortical neuronal cultures using SNOC. To assay whether this protection from cell death was due to nitration of proteins, cultures were probed using an antibody specific for the addition of a nitro ($-NO_2$) group on the position 3 of tyrosine residues (3-NT). As seen in representative images, an increase in of 3-NT signal in SNOC treated cortical neurons was seen (FIG. 5A center right panel) whereas treatment of neuronal cultures with $CeO_2$ NPs reduced the 3-NT signal (FIG. 5A far right panel). These cultures were scored for cell death and it was observed that treatment with $CeO_2$ NPs rescued the SNOC treated cultures from cell death (FIG. 5B). This data was corroborated when images were assessed by semi-quantitative immunofluorescence. A decrease in the 3-NT signal in cultures pretreated with $CeO_2$ NPs was detected (FIG. 5C). These results indicate a protective effect afforded by the $CeO_2$ NPs ability to scavenge $ONOO^-$.

Relative nitrotyrosine immunoreactivity was analyzed in cortical neuronal whole cell lysates. Positive 3-NT labeling of SNOC treated lysates showed many potential biological targets were nitrated. However, as measured by densitometry, pretreatment with $CeO_2$ NPs abrogated the 3-NT formation (FIG. 5D). This demonstrates $CeO_2$ NPs may act by attenuating the damaging effects of $ONOO^-$ by reducing 3-NT modification of brain proteins. Together, this data shows that nitration of tyrosine residues mediated by $ONOO^-$ can be abolished by the antioxidant properties of $CeO_2$ NPs.

Figure 6A:
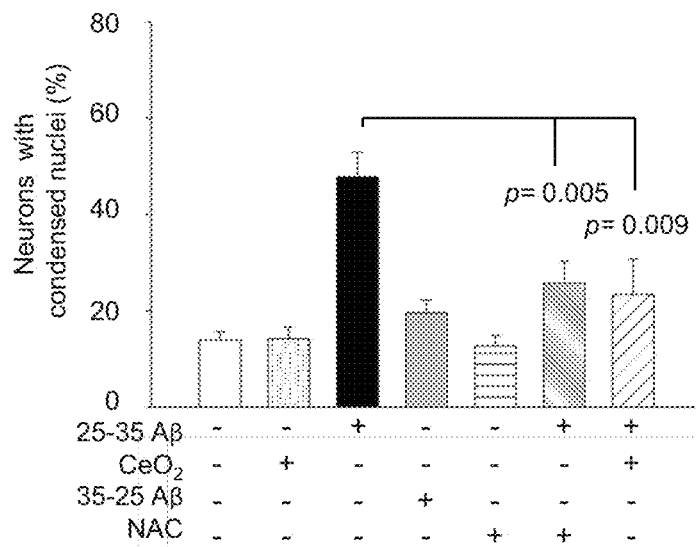
FIG. 6A is a table showing $CeO_2$ NPs increasing cell viability from Aβ treatments.

Example 7: $CeO_2$ NPs Increase Cell Viability from Aβ Treatments and Attenuate Aβ Oligomerization The amyloid precursor protein (APP) and its cleavage products are thought to trigger a series of events that result in neurodegeneration. The increased production of Aβ and the incorporation into oligomers with subsequent deposition into plaques has been correlated with the progression of AD (46). Aβ (25-35) peptide is found in senile plaques and degenerating hippocampal neurons in AD brains but not in age-matched control subjects (47). Aβ (25-35) is the shortest peptide sequence that retains biological activity and exhibits large β-sheet structures (48). The Aβ (25-35) peptide very rapidly aggregates (49) and was allowed to oligomerize at RT for 24 h (5) before adding to pure neuronal cultures. The Aβ (25-35) treatment led to significant reduction in cell viability which was relieved by pretreatment with $CeO_2$ NPs in a manner that similar to pretreatment with NAC (FIG. 6A). The reverse peptide, Aβ (35-25) had no effect on cell death. This exposure to oligomerized Aβ is dependent upon the NMDA type receptor activity (9) which leads to increased nitrosative stress through activation of nNOS (50). These results show that $CeO_2$ NPs treatment protects neurons against acute Aβ-induced nitrosative stress.

Figure 6B:
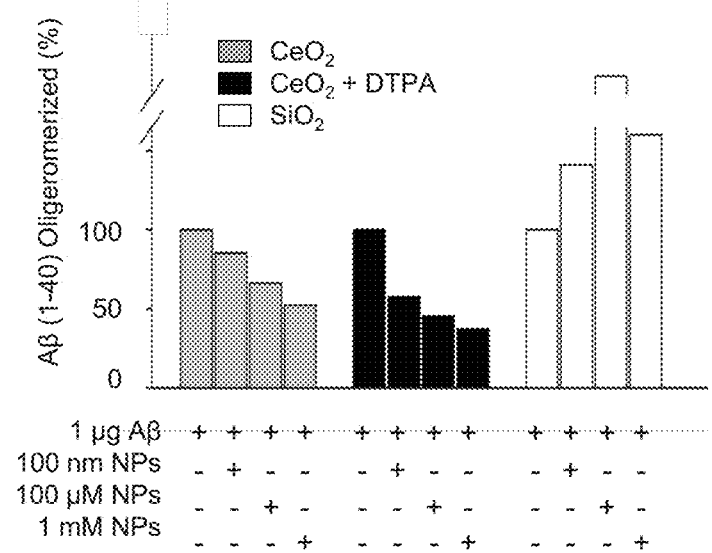
FIG. 6B is a table showing $CeO_2$ NPs attenuate Aβ oligomerization.

The plaques of AD patients consist of accumulated Aβ (1-40) and Aβ (1-42) (51) and these are widely believed to contribute to neurotoxicity and AD pathogenesis. The neurotoxicity of the Aβ peptides is due at least in part to the production of ROS through metal ion reduction (52). To test whether $CeO_2$ NPs could impart protection against β-amyloid fibril formation, 1 μg of Aβ (1-40) peptide was allowed to oligomerize for 7 days in the presence of increasing amounts of $CeO_2$ NPs and oligomer formation was analyzed using a protocol modified from Kayed et al. (53). The peptides were then dot blotted onto nitrocellulose and probed with an antibody which recognizes the oligomeric and not the monomeric form. Densitometric analysis of the dot blot shows Aβ fibril formation was attenuated with addition of increasing amounts $CeO_2$ NPs (FIG. 6B). In contrast, $SiO_2$ NPs did not affect the oligomerization. These results indicate $CeO_2$ NPs, even in the presence of the metal chelator diethylenetriaminepentaacetic acid (DPTA), were able to inhibit the formation of β-amyloid fibrils. Therefore, the protective role of the $CeO_2$ NPs in protection against β-amyloid toxicity is likely to be a combination of ROS and RNS scavenging properties.

Example 8: Nanoceria Protect Against Aβ-Induced Mitochondrial Fragmentation

Nitrosative stress plays an important role in Aβ-mediated neurotoxicity (94, 95). Aβ or nitrosative stress evoke persistent mitochondrial fragmentation, an event that causes bioenergetic failure, impaired $Ca^{2+}$ homeostasis, synaptic injury, axonal transport defects, and neuronal cell death (5, 96). To test whether nanoceria would prevent the Aβ-induced mitochondrial fragmentation, the mitochondrial morphology by fluorescence microscopy in neurons expressing DsRed2-Mito, a red fluorescent protein targeted to the mitochondrial matrix was visualized. Control neurons, —either left untreated or treated with nanoceria alone (3 h pretreatment)—, demonstrated an elongated mitochondrial morphology, typical of healthy neurons (FIGS. 7a(a) and 7a(b)). By contrast, oligomeric Aβ25-35 peptide, but not the reverse Aβ35-25 control peptide (FIG. 7a(g)), induced dramatic mitochondrial fragmentation evidenced by the appearance of mitochondria with mostly round morphology (FIG. 7a(c)). Remarkably, nanoceria prevented the Aβ25-35-induced mitochondrial fragmentation, similar to N-acetyl-L-cysteine (NAC), a known NO/ONOO⁻ neutralizing antioxidant supplement (FIGS. 7a(d) and 7a(f)). Further quantitative analysis demonstrated that nanoceria significantly reduced the Aβ-induced mitochondrial fragmentation in neurons (FIG. 7b). These results suggest that nanoceria not only accumulate at mitochondria, but can also preserve their morphology and function in response to neurotoxic insults such as A3.

Example 9: Nanoceria Reduce DRP1 Phosphorylation at 5616

Figure 8A:
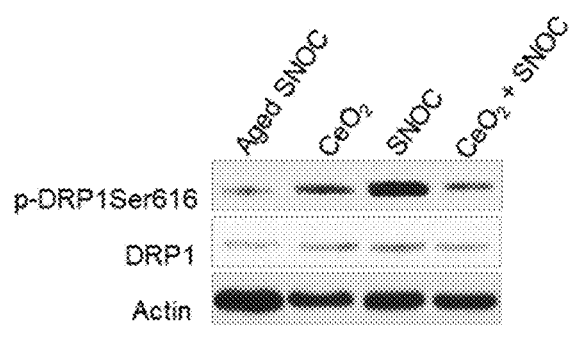
FIGS. 8A-8B Nanoceria abolish DRP1 phosphorylation at S616 in response to RNS.
Figure 8B:
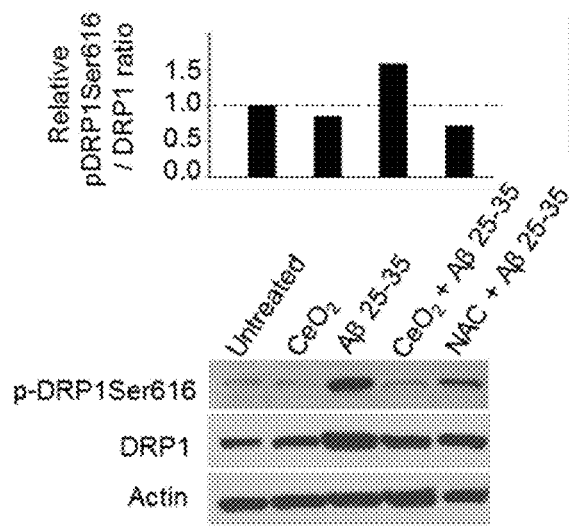

There is increasing evidence that mitochondrial fragmentation, owing to excessive DRP1-dependent mitochondrial fission, plays a central role in many neurodegenerative disorders including AD (87). Cdk1/cyclinB1-mediated phosphorylation of DRP1 at 5616 causes its recruitment from the cytoplasm to mitochondria to initiate organelle division in mitotic cells (88). However, all Cdk's are inactivated in postmitotic neurons with the exception of Cdk5. Over-activation of NMDA receptors by Aβ triggers excessive nitrosative stress and cytoplasmic $Ca^{2+}$ levels. (20) possibly leading to increased NO production. SNOC triggers DRP1 S616 phosphorylation and mitochondrial fragmentation (5, 86). Notably, p-DRP1 S616 is increased in AD patient brains (86, 90, 97). Because nanoceria prevented Aβ-induced mitochondrial fragmentation (FIG. 7), it was questioned whether they might inhibit DRP1 S616 phosphorylation, providing an explanation for the preservation of mitochondrial morphology by nanoceria. Neurons treated with either aged SNOC or nanoceria alone exhibited only low baseline DRP1 S616 phosphorylation (FIG. 8a). By contrast, neurons treated with fresh SNOC exhibited high p-DRP1 S616 levels (FIG. 8a). Remarkably, nanoceria significantly reduced the SNOC-induced increase in DRP1 S616 phosphorylation (FIG. 8a). Similarly, nanoceria or NAC abolished the Aβ 25-35-induced DRP1 S616 phosphorylation (FIG. 8b). These results suggest that nanoceria reduce nitrosative stress or Aβ-induced mitochondrial fragmentation perhaps by preventing DRP1 S616 hyperphosphorylation.

Example 10: Nanoceria Protect Against Aβ-Induced Neuronal Cell Death

Figure 9A:
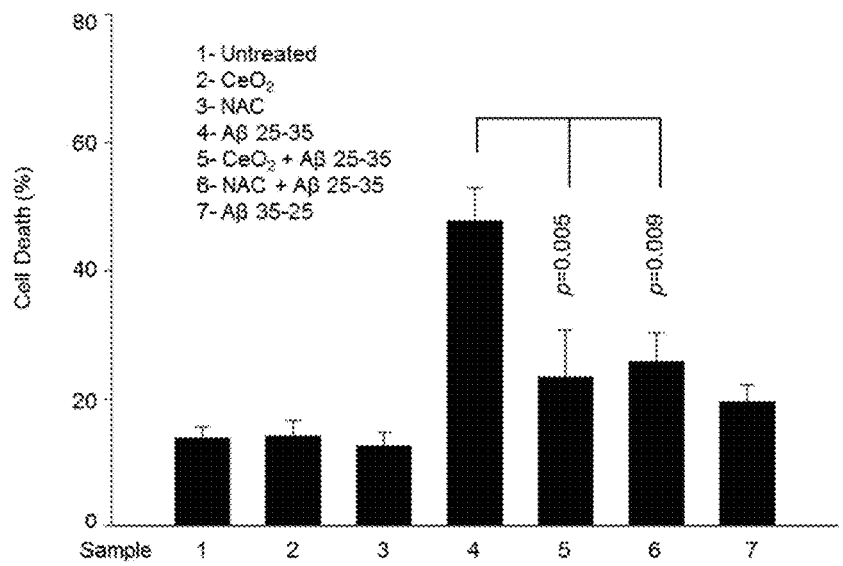
FIGS. 9A-9D Nanoceria delay neuronal cell death induced by Aβ, NMDA, glutamate, or 3-NP.
Figures 9B, 9C, 9D:
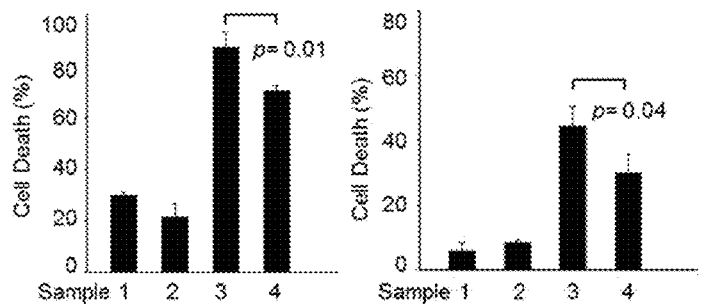
Figures 10A, 10D:
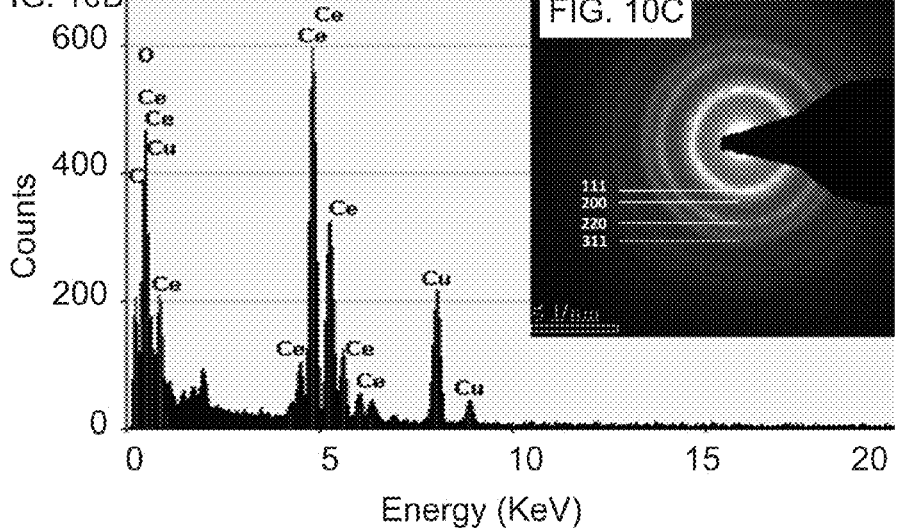
Figure 11:
FIG. 11. $CeO_2$ NPs in cortical neurons. TEM section without post-stain assures that the dense particles are from addition of $CeO_2$ NPs and not due to staining artifact.
Figure 12A:
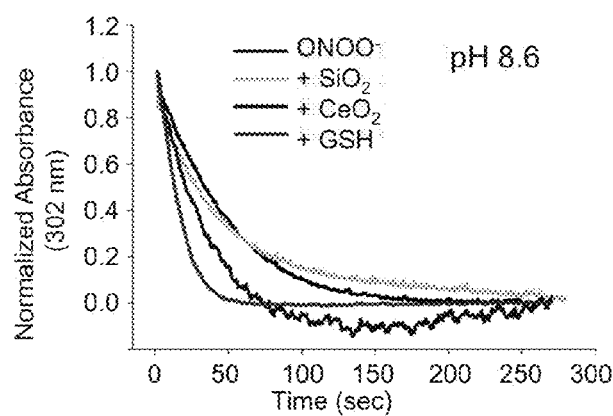
FIGS. 12A-12B: Effect of $CeO_2$ NPs on the rate of decay of $ONOO^-$ in vitro varying pH. $ONOO^-$ (25 μM) was added at various pH's alone and in the presence of $CeO_2$ NPs (100 μM), $SiO_2$ NPs (100 μM), glutathione (GSH) (0.5 mM).
Figure 12B:
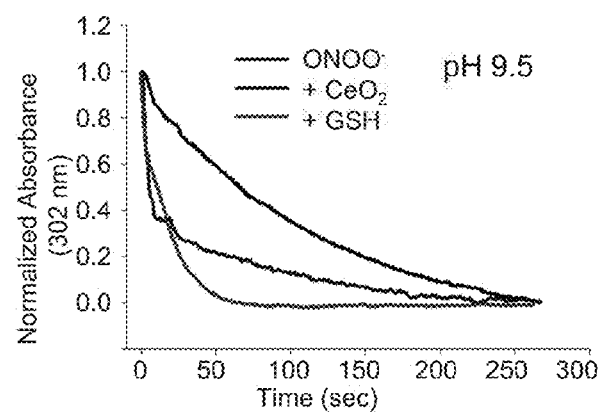

Cell death by Aβ or NMDA occurs, at least in part, through endogenous RNS/ROS (5). Neuronal death by the complex II inhibitor 3-nitropropionic acid (3-NP) triggers secondary excitotoxicity and RNS/ROS (30). Aβ25-35, but not the reverse peptide, elicited neuronal cell death, which was reduced in the presence of either nanoceria or NAC (FIG. 9a). Similarly, neuronal cell death by excess NMDA or glutamate was reduced by nanoceria (FIGS. 9b and 9c). Finally, similar neuroprotective effects were observed against respiratory complex II inhibition by 3-NP (FIG. 9d). Thus, nanoceria provide neuroprotection against a variety of insults that generate endogenous ROS/RNS.

A mode of action for the way in which $CeO_2$ NPs may attenuate RNS in cells which could have far reaching implications in neurodegenerative diseases has been described herein. In the present study, $CeO_2$ NPs were investigated and it was found that they were able to mediate neuroprotection by decreasing RNS, and in one particular embodiment, ONOO⁻. First, TEM analysis shows the incorporation of $CeO_2$ NPs by cortical neurons. TEM showed the association of $CeO_2$ NPs with membranes, both mitochondrial and plasma. These locations align with the primary sources of reactive nitrogen species in neurons. Sites of ONOO⁻ formation also include the mitochondrial membrane, due to the mitochondrial respiratory complexes, and plasma membrane NADPH oxidases.

The biochemistry of ONOO⁻ is vastly complicated due to the multiple reactions possible in the presence and absence of $CO_2$, $H^+$ and metals during its decomposition (54, 55). Given its redox active nature, the interaction of $CeO_2$ NPs and ONOO⁻ was studied in vitro to improve the understanding of its biological capabilities. In vitro data using 302 nm absorbance and APF fluorescence assays were used to demonstrate that these $CeO_2$ NPs can speed the decomposition of ONOO⁻. This is decay held up even at higher pHs which may come into play when considering molecules that depend on tyrosine for their function. The pKa of the nitro-tyrosine (7.4) is considerably lower than tyrosine (10.07) (56). The nitration of the phenolic ring can inactivate enzymes and/or receptors that rely on phosphorylation of tyrosine for signaling. This newly identified catalytic property of $CeO_2$ NPs strengthens the evidence for the antioxidant properties (19, 20, 25).

The biological significance of $CeO_2$ NPs interaction with ONOO⁻ was then demonstrated. Oxidative and nitrosative stress occurs due to an imbalance of antioxidants and antioxidant enzymes to oxidants. Neurons have a high energy demand and contain several hundred mitochondria per cell and therefore have increased exposure to ROS and RNS (13). Though it cannot be ruled out that $CeO_2$ NPs are acting in addition as SOD mimetics, mitochondria are a primary site of the intercellular formation of ONOO⁻ (45) making neuronal cultures and by extension, neurodegenerative diseases an optimal prototype for exploring the biomedical applications of $CeO_2$ NPs.

Over-activation of the glutamate receptors has been linked to a number of disease conditions including neurodegenerative diseases such as Huntington's diseases (HD), Parkinson's disease (PD), amyotrophic lateral sclerosis (ALS) and Alzheimer's disease (AD) (1). The excitatory amino acid glutamate has key roles in development of neurons and neurodegeneration through the activation of NMDA receptors which leads to increased oxidative and nitrosative stress (57). It has been discovered herein that treatments of cortical neurons with CeO2 NPs were able to protect from a variety of stressors, all of which increase RNS. These included treatments with 3-NP, glutamate, NMDA and Aβ peptide (25-35). The common molecular link between these conditions is an increase in production of ONOO⁻. In the case of 3-NP, a complex II inhibitor, depolarization of the mitochondrial membrane occurs followed by the rapid decrease of ATP, leads to an increase of NO. via the opening of the NMDA receptors (30). The NO. and increased $O_2^{\cdot-}$ from the mitochondria lead to rising $ONOO^-$ levels. Likewise, excess glutamate and NMDA can lead to NMDA receptor activation and with a subsequent increase in free radical production leading to increased $ONOO^-$. Increased levels of $ONOO^-$ levels then affect all biological molecules eventually causing neuronal dysfunction or death. Similarly, application of synthetic Aβ can modulate NMDA receptors (9). Aβ triggered neuronal dysfunction can also increase $ONOO^-$. Aβ half-life in the central nervous system is normally 2 h but in AD, the half-life is increased due to altered clearance, therefore allowing increased chance of oligomerization. It has been found that $CeO_2$ NPs prevented the aggregation of the Aβ (1-40) peptide even in the presence of the metal chelator DPTA. This is important since many current therapeutic strategies use metal chelators to alter the progression of AD symptoms (58). Not only can $CeO_2$ NPs reduce the fibril formation in vitro but also the cell death caused Aβ (25-35) nitrosative stress. The findings provided herein are of broad significance in the search for an $ONOO^-$ scavenger to inhibit the progression of neurodegenerative disorders, such AD, in which nitrosative stress plays a key role.

The results provided herein show that $CeO_2$ NPs protected cortical neurons from multiple nitrosative neuronal stressors. The intercellular location of the $CeO_2$ NPs likely enhances the scavenging of $ONOO^-$. To further understand the mechanism of neuronal protection seen by $CeO_2$ NPs, $ONOO^-$ and its ability to promote the nitration of tyrosine residues was considered. Specific nitrated proteins, such as, for example, Tau and the neurofilament light subunit (NF-L) have been heavily reported in literature to be linked to AD (59, 60). Modification of key proteins may result in detrimental change in function of the proteins. Tyrosine nitration modification of proteins has become an important marker for inflammation and has been detected in a number of diseases and pathological conditions (4). Disproportionate amounts of NO. can complete with oxygen causing the interruption of electrons from the respiratory chain which results in increased formation of $O_2^{\cdot-}$ (4) and thus increased $ONOO^-$ leading to the post-translational modification of proteins. Increased levels of nitrated proteins have been reported in AD brains as well as cerebrospinal fluid in patients with AD (61). Reduction of nitrosative injury by $CeO_2$ NPs will lead to better therapeutic success of AD and reduction of neurodegeneration.

The results obtained in this study were the first to demonstrate that $CeO_2$ NPs can alter the decomposition of $ONOO^-$, a newly identified and catalytic activity for $CeO_2$ NPs. $CeO_2$ NPs ability to readily react with $ONOO^-$ has wide ranging implications for neurodegenerative disorders and aging. Once formed in the brain, $ONOO^-$ can exert its toxic effects in many ways. Nitrotyrosine immunoreactivity has been implicated in the early stages of many diseases, including AD, PD, HD, multiple sclerosis (MS), and ALS (62-65). Widespread $ONOO^-$ damage in AD has been demonstrated in many studies (7, 66). The ability of $CeO_2$ NPs to protect from these putative causative agents in AD, both cell death from Aβ peptide stress and 3-NT modifications by $ONOO^-$ provides compelling rationale for further study into the molecular basis of this protection in diseases for which RNS may play a key role.

Moreover, nitrosative stress can activate kinases (74, 75). Specifically peroxynitrite can activate p38 MAP kinase and Cdk5 (76). Neurotoxic signals including Aβ and excess glutamate or NMDA causes an impaired $Ca^{2+}$ homeostasis, which can activate downstream mediators including NOS and calpain (82). ROS/RNS can directly activate Cdk5. Aberrant Cdk5 activation in neurodegeneration can occur by two mechanisms. First, nitrosative stress can directly activate Cdk5 by increasing its phosphorylation. Second, $Ca^{2+}$-dependent calpain cleavage of the Cdk5 activator p35 to p25 increases its stability. Consequently, Cdk5/p25 is constitutively activated. (77, 78, 79, 80). The blockage of mitochondrial fragmentation by nanoceria in response to Aβ was associated with a reduction in DRP1 S616 hyperphosphorylation (FIG. 8b). Although it is unlikely that nitrosative stress mediates mitochondrial fragmentation and neuronal cell death only by phosphorylating a single protein target, such as DRP1, the present data describes one possible mode of action how nanoceria may specifically attenuate the downstream effects of RNS/ROS.

Most therapeutic treatments of AD have targeted reducing or clearance of Aβ with disappointing results however, therapeutic strategies aimed at reducing mitochondrial damage, especially through mitochondrial antioxidants (81) show promise. Considering nanoceria's proximity to mitochondria they may be uniquely situated to protect neurons in AD from nitrosative stress and mitochondrial dysfunction by lowering DRP1 S616 phosphorylation and thereby maintaining bioenergetic function and neuronal viability.

Nanoceria have been shown to decrease RNS/ROS-induced damage by many stress stimuli and in several cellular and animal models (20). No toxicity or adverse effects to nanoceria in the eyes of rats was found, where it prevents vision loss due to increased ROS from excess light exposure (19). Nanoceria also mitigate ischemic brain injury where nanoceria markedly decreased the levels of 3-nitrotyrosine (3-NT) (82) In addition, nanoceria accumulated on mitochondria, consistent with the provided results. The small size of nanoceria allowed passage into the neurons, but delivery routes into all cell types and tissues must still be tested. These are not trivial issues, yet considering the results that nanoceria protected cortical neurons from multiple nitrosative-associated stressors, they represent a potential exciting alternative strategy compared to traditional antioxidants. The present studies represent an important step forward to test the potential neuroprotective effects of nanoceria in in vivo animal models of AD.

Materials and Methods for Examples 1-10

Reagents

EBSS (Earle's Balanced Salt Solution), Hank's buffer, Glutamax, B27, LipoFectamine2000®, and penicillin-streptomycin were purchased from Invitrogen (Carlsbad, Calif.). Neurobasal medium, Dulbecco's Modified Eagle's Medium (DMEM) was purchased from Hyclone (Logan, Utah). Poly-L-lysine, HEPES, glutamine, formaldehyde, N-acetyl-L-cysteine (NAC), anti-MAP2 antibodies (clone HM-2), anti-3-nitrotyrosine (3-NT), N-methyl-D-aspartate (NMDA), Ponceau S reagent, Durcupan ACM, 3-nitropropionic acid (3-NP), all Aβ peptides and all the chemicals for $CeO_2$ NPs synthesis were obtained from Sigma-Aldrich (St. Louis, Mo.). Hoechst 33342, AlexaFlour488, AlexaFluor594, pluronic acid, 3'-(p-aminophenyl) fluorescein (APF) (for cell culture), anti-β-actin antibody and PVDF membrane were purchased from Molecular Probes (Invitrogen). The DsRed2-Mito vector was obtained from Clontech (Mountain View, Calif.). Vector Shield was purchased from Vector Laboratories, Inc., (Burlingame, Calif.). T-Per extraction reagent was purchased from Pierce Biotechnology, Inc., (Rockford, Ill.). Nitrocellulose (Hybond) for dot blots and anti-mouse and anti-rabbit HRP-conjugated secondary antibodies came from ECL/GE Healthcare (Piscataway, N.J.).

Peroxynitrite (ONOO−) and 2-[6-(4-aminophenoxy)-3-oxo-3H-xanthen-9-yl]-benzoic acid (APF) (for in vitro experiments) were purchased from Cayman Chemicals (Ann Arbor, Mich.). All reagents for transmission electron microscopy (TEM) were purchased from Ted Pella (Redding, Calif.). $SiO_2$ nanoparticles were purchased from Corpuscular Inc. (Cold Spring, N.Y.). In addition the following antibodies were used: monoclonal mouse-anti-DRP1 antibodies (clone 8/DLP1, BD Bioscience), rabbit polyclonal anti-p-DRP1 S616 antibodies (Cell Signaling), rabbit polyclonal 3-nitrotyrosine (Sigma), rabbit β-actin antibody (Cell Signaling); sheep-anti-mouse IgG-HRP (GE Healthcare), donkey-anti-rabbit IgG-HRP (GE Healthcare), goat-anti-mouse AlexaFluor488 (Invitrogen), goat-anti-rabbit AlexaFluor594 (Invitrogen).

Primary Neuronal Cultures

Purified or mixed cortical cultures were prepared from E18 rat embryos. Cells (400,000 cells/ml cell density) were plated in D10C medium (DMEM, 10% bovine calf serum, 2 mM glutamine, 25 mM HEPES, 10% F-12, and 0.25% penicillin-streptomycin) on poly-L-lysine (1 mg/ml) coated dishes. For pure cultures, the medium was replaced after 4 h with neurobasal medium supplemented with 2% B27, 2 mM Glutamax, and 1% penicillin-streptomycin. For live-cell imaging, phenol red-free neurobasal growth medium was used. Cultures were maintained at 37° C. in a humidified 5% $CO_2$ atmosphere and fed every 3-4 days as previously described (5, 30).

Scoring for Cell Death

Cultures were either transfected with DsRed2-Mito on day 5 using LipoFectamine2000® or immunostained for microtubule-associated protein 2 (MAP2) for visualization of processes. Experiments were performed after 11-14 days in vitro (DIV) with 3-NP, glutamate or NMDA. SNOC treated cultures were performed after 8 DIV. Neurons were pretreated with $CeO_2$ NPs for various time points, 3 h, 12 h, 24 h or 72 h. For cultures treated with 3-NP (diluted in EBSS and pH adjusted to 7.4 with NaOH), 3-NP was diluted in individual culture's conditioned medium before exchange and cultures left for 8 h. Brief exposure to NMDA was carried as follows. Culture medium was removed and saved and cultures washed with pre-warmed treatment buffer (1.8 mM $CaCl_2$, 5 µM glycine in EBSS). Cells were exposed to NMDA (150 µM or 200 µM) for 20 min, washed with treatment buffer, conditioned media returned and then left for 12 h. Alternately, cells were treated with glutamate at various concentrations; 50 µM (13 h), 100 µM (4-6 h) or 150 µM (4-6 h). For Aβ (25-25) treated cultures, Aβ (25-35) or reverse (35-25) was left to oligomerize for 24 h at 25° C. before adding to cultures at 10 µM for 6 h. Cells were fixed in 3.7% formaldehyde and 5% sucrose in PBS for 20 min at 37° C. (to preserve mitochondrial morphology) or 4% paraformaldehyde for immunostaining. Cover slips were mounted with Vector Shield and sealed. Analyses were performed on triplicate coverslips of at least three independent experiments. Cells with fragmented mitochondria and condensed chromatin by Hoechst 33342 staining were scored as dead neurons. To evaluate mitochondrial fragmentation and cell death of a large number of neurons, manual scoring was carried out of neurons grown on glass coverslips using conventional fluorescence microscopy.

Mitochondrial Fragmentation and Neuronal Cell Death

Neurons were grown on poly-Lysine coated glass cover slips as described before and transfected with DsRed2-Mito after 5 days in vitro (DIV) using Lipofectamine2000®.

Where indicated, neurons were pretreated with nanoceria for 3 h. 3-NP was prepared as previously described (30). The Aβ peptides were preaggregated as described before (5). Cell death was induced with 3-NP (10 mM, 8 h), glutamate (150 µM, 6 h), NMDA (150 µM, 12 h) Aβ (10 µM, 6 h) at 11-14 DIV or with SNOC (100 µM, 3 h) at 8 DIV. After various time periods neurons were fixed using 3.7% formaldehyde and 5% sucrose in PBS for 20 min at 37° C. Nuclei were labeled with Hoechst 33342 (1 µg/ml). Quantification of mitochondrial fragmentation and neuronal cell death was performed as described (30). Fluorescence microscopy and image acquisition of mitochondrial morphology was performed as previously described (98).

Immunocytochemistry

For immunocytochemistry, cortical cultures grown on glass coverslips were fixed in 4% formaldehyde in PBS buffer (pH 7.0; 20 min; 42° C.) and then permeabilized with 0.1 or 4% Triton X-100 in PBS (pH 7.4; 5 min; room temperature (RT)). Nonspecific binding was blocked with 3% BSA, 3% FBS in PBS for 1 h at room temperature. Cells were then probed with 3-NT (1:500) (RT, 2 h), and/or an antibody specific for MAP 2 protein (1:200) (RT, 2 h), a neuronal marker followed by a conjugated fluorescent secondary antibodies AlexaFluor594 or AlexaFluor488 (respectively) at dilutions of 1:500 (RT, 2 h). Chromatin was stained by incubating fixed samples with Hoechst 33342 (1 µg/ml) at RT for 20 min. For 3-NT, immunostaining conditions were first optimized along with a blocking control, using 10 mM nitrotyrosine, to confirm specificity of 3-NT signal (31).

To visualize 3-NT using AlexaFluor594, the excitation filter was 5555/28× (Chroma) and the emission filter was 5617/73m (Chroma), to visualize neurons using AlexaFluor488, the excitation filter was 5490/20× and the emission filter was 5528/38m (Chroma) and to visualize Hoechst 33342 the excitation filter was 5403/12× and emission filter 5475/50m. Immunostaining conditions for 3-NT were first optimized along with a blocking control, using 10 mM nitro-tyrosine, to confirm specificity of 3-NT signal. Fluorescence microscopy was performed as previously described (84). Quantification of fluorescence from 3-NT was as follows. Exposure time, brightness and contrast of randomly selected cortical neurons were held constant for all images within same experiment. Using MetaMorph 7.5, a region of interest was selected around each neuron using the MAP 2 label as a guide. This region was transferred to the 3-NT image channel. The fluorescence intensity for each neuron was measured using Show Region Statistics function. Area and intensity/fluorescence data was logged for each neuron. Twenty five to fifty neurons from each treatment were evaluated for a total of over 100 neurons per experiment. Three areas were selected randomly within each image and the average of their fluorescence intensity was considered as background. The background was subtracted within each image. 3-nitrotyrosine immuno-fluorescence quantification is expressed as fluorescence per $\mu m^2$.

Image Analysis

Fixed cell imaging was performed using an Axiovert Zeiss 100M inverted fluorescent microscope equipped with a plan Apochromat 63×1.4 NA oil objective, a DG-4/Lambda 10-2 combo Xe-arc illumination unit (shutter), and a Sensicam QE cooled CCD camera (PCO AG, Germany) controlled by MetaMorph 7.1 software (Molecular Devices). To visualize DsRed2-Mito and AlexaFluor594, the excitation filter was 5555/28× (Chroma) and the emission filter was 5617/73m (Chroma). To visualize AlexaFluor488, the excitation filter was 5490/20× (Chroma) and emission filter was 5528/38m (Chroma). To visualize Hoechst staining for the nucleus, the emission filter was 475/50m (Chroma).

Three dimensional images were acquired with the Multi Dimensional Acquisition module, 2×2 binning, 0.2-0.5 mm step size, and stacks of 10-21 z-planes.

Live Cell Imaging of Peroxynitrite

Neurons were seeded on MakTek petri dishes treated with poly-L lysine. For generation of ROS/RNS, the cultures were exposed to freshly prepared S-nitrosocyeine (SNOC) (50-200 µM), or aged SNOC (as control) for 2 h. To visualize ONOO$^-$, neurons (+/− CeO$_2$ NPs) were loaded with imaging buffer (neural basal supplemented with 0.2% pluronic acid, 1.8 mM CaCl$_2$, 0.8 mM MgCl$_2$) containing 2% APF also containing 1:10,000 Hoechst dye 33342 (1 µg/mL) for 30 min at 37° C. Dye was removed and replaced with conditioned phenol red-free NB medium. Fluorescence intensity was monitored in response to addition of SNOC. Z-stacks were acquired keeping exposure time, brightness and contrast constant for all images. Images were taken with 40× or 63× oil immersion objective lens and stored as tif files as visualized by excitation filter 5490/20× (Chroma) and emission filter 5528/38m (Chroma). From each sampled imaged, the number of APF positive cells were quantified by two independent methods: 1.) Manual scoring for presence of uncondensed nuclei or condensed nuclei with presence of dye; 2.) Using MetaMorph 7.5 software (Molecular Devices), equal backgrounds were subtracted from each z-stack image (as determined from control) then pixels from each z-stack series was summed. Cell soma and processes were selected and the number of pixels quantified per µm$^2$. This region was transferred to the APF image channel. The fluorescence intensity for each neuron was measured using Show Region Statistics function. Intensity/fluorescence data was logged for each neuron and data exported to Excel for further analysis.

Preparation of CeO$_2$ Nanoparticles

The ceria nanoparticles were synthesized by wet chemical process as previously described (32). In brief, for preparation of CeO$_2$ NPs with increased ratio of 3$^+$/4$^+$, Ce(NO$_3$)$_3$·6H$_2$O was dissolved in dH$_2$O and H$_2$O$_2$ was rapidly added with stirring at 300 rpm. The solution was then heated at 150° C. with continuous stifling to obtain a light yellow colored stable dispersion of cerium oxide nanoparticles. All CeO$_2$ NPs were sonicated (Branson, Danbury, Conn.) to prevent agglomeration for 45-60 min prior to use.

Western Blotting

To detect protein nitration, neurons were lysed using T-Per extraction reagent (Pierce) supplemented with Complete Protease Inhibitor Cocktail (Roche Applied Science, US). Protein concentrations were determined using the Bradford assay (Pierce Biotechnology, Inc., Rockford, Ill.). Proteins were separated by 4-20% SDS-PAGE gradient gels (Invitrogen) and transferred to PVDF membranes (0.2 µm, Bio-Rad). Nonspecific protein binding was blocked by incubating the membranes with TBS (50 mM Tris-Cl, pH 8.0, 150 mM NaCl), 0.02% Tween20, and 5% nonfat milk for 3 hours at room temperature. The membranes were then probed with primary rabbit polyclonal antibodies for 3-nitrotyrosine (Sigma) (1:500) overnight at 4° C. After four washes (5 min) of TBS (0.02% Tween20), membranes were incubated for two hours at room temperature with anti-rabbit horseradish peroxidase-conjugated secondary antibodies (GE Healthcare) (1:15,000) in blocking solution. After four washes (5 min) of TBS (0.02% Tween20), immunocomplexes were detected using the Super-Signal West-Dura chemiluminescence substrates (Pierce, Thermo Scientific, Rockford, Ill.). Restore Western Blot Stripping Buffer (Thermo-Scientific) was used to strip blots. Membranes were successively probed with anti-β-actin antibody (Cell Signaling, 1:1000).

To measure the levels of p-DRP1 S616, neurons were lysed in buffer containing 50 mM Tris-Cl, pH 7.0, 150 mM NaCl, 1 mM MgCl$_2$, 1 mM NaF, 1 mM NaVO$_4$, 1% NP40, 10% glycerol and complete Protease Inhibitor Cocktail Tablets (Roche Applied Science, US). Membranes were blocked with 5% nonfat milk in TBS (pH 8.0) with 0.05% Tween20 for 3 h at room temperature (RT) and were incubated with primary rabbit polyclonal antibodies for p-DRP1 S616 (Cell Signaling) (1:1000) overnight at 4° C. The membranes were then washed four times (5 min) with TBS (0.05% Tween) and incubated for 2 h at room temperature with anti-rabbit horseradish peroxidase-conjugated secondary antibodies (GE Healthcare)(1:15,000) in blocking solution. After 4 washes (5 min) of TBS (0.05% Tween), immunocomplexes were then detected using the Super-Signal West-Dura or Femto chemiluminescent substrates (Pierce, Thermoscientific, Rockford, Ill.). For re-probing the membranes were stripped with Restore Western Blot Stripping Buffer (Thermo-Scientific) according to the manufacturer and incubated with mouse monoclonal antibodies for DRP1 (BD Biosciences, clone 8/DLP1) (1:1000) antibody or with polyclonal rabbit antibodies for β-actin (Cell Signaling) (1:1000).

3-Nitrotryosine Detection Using Western Blot

Analysis of proteins for nitrotyrosine modification were isolated from mixed or pure neuronal cultures (8 DIV) after SNOC treatment +/−CeO$_2$ NPs using T-Per extraction reagent according to the manufacturer's recommendations, with the addition of the cOmplete Protease Inhibitor Cocktail Tablets (Roche Applied Science, US). Protein concentrations were determined using the Bradford assay (Pierce Biotechnology, Inc., Rockford, Ill.). To detect and for Western blot analysis, 25 µg of protein were fractionated by 4-20% SDS-PAGE gradient gels and transferred to PVDF membrane. Equal loading was evaluated by staining membranes with Ponceau S reagent and re-probing of blot using anti-β-actin antibody (1:1000).

Polymerization Dot Blot Assay

Aβ (1-40) oligomer (Sigma) was prepared with sterile H$_2$O. The final Aβ concentration was 1 mg/ml. CeO$_2$ and SiO$_2$ NPs were added to 1 µg Aβ solutions to give final 100 nM, 100 µM and 1 mM. The samples were incubated for 7 d at 25° C. undisturbed. Samples were applied to nitrocellulose membrane in a Bio-Dot apparatus (Bio-Rad). The membrane was blocked with 10% nonfat milk in TBS-T at room temperature, washed with TBS-T, and probed with anti-oligomer A11 antibody solution (1:1,000) in 3% BSA-TBS-T overnight at 4° C. After washing, it was probed with anti-rabbit horseradish peroxidase-conjugated antibody (Pierce) solution (1:15,000) for 1 h at room temperature. For detection, West Dura substrate (Thermo Scientific, Rockford, Ill.) was used as per manufacture protocol and blots exposed to film (Hyperfilm; Amersham Pharmacia Corp.). The signals were quantified by densitometry using Image-J Software. The amount of oligomerization detected was normalized to the amount of background signal by NPs alone to yield a normalized estimate for the Aβ (1-40) oligomerization.

Monitoring Peroxynitrite In Vitro

ONOO$^-$ (20 µM) was added to APF along with varying amounts CeO$_2$ NPs. Glutathione (Fisher, Fair Lawn, N.J.) and uric acid (Avocado, Research Chemicals, Ltd.) known scavengers of ONOO$^-$, were used as positive controls.

Fluorescence at 515 nm (ex. 490 nm) was measured using a Varian Cary Eclipse fluorescence spectrophotometer (Palo Alto, Calif.).

Monitoring Peroxynitrite Levels by UV-Visible Spectroscopy

UV-visible spectroscopy was used to measure decomposition of $ONOO^-$ in the presence and absence of $CeO_2$ NPs. $ONOO^-$ (20 µM) was added, while stifling, into a 1 mL quartz cuvette with a 1 cm path length. Each sample was analyzed for a total of 600 seconds with a cycle time of 0.5 seconds at a wavelength of 302 nm using buffer containing 100 mM sodium phosphate buffer (pH 9.5-8.0) and 1 µM diethylenetriaminepentaacetic acid (DPTA) with or without $CeO_2$ NPs. Spectrophotometric data was collected using a Hewlett-Packard diode array UV-visible 8453 spectrophotometer.

Transmission Electron Microscopy

Neurons were seeded on MakTek petri dishes coated with poly-L lysine. Cultures 11 DIV were treated with 100 nM $CeO_2$ NPs for 3 h, 12 h and 24 h. Neurons were fixed in 2% paraformaldehyde, 0.15 M sodium cacodylate, pH 7.4 and 2.5% glutaraldehyde for 5 min RT followed by 30 min on ice. Cultures were washed in ice cold 0.15 M sodium cacodylate and 3 µM calcium chloride 3×3 min on ice followed by post-fixation in 1% osmium tetroxide, 0.8% potassium ferricyanide, 3 µM calcium chloride in 0.15 M sodium cacodylate for 60 min on ice. After 3 washes in ice-cold $ddH_2O$ (3 min), cultures were stained in 2% uranyl acetate for 30 min. Samples were dehydrated in ethanol series of ice-cold 20, 50, 70, 90 then 3 washes in 100% ethanol at RT for 3 min at final step. Samples were first infiltrated in 50% ethanol/50% Durcupan ACM (Fluka/Sigma) for 1 h at RT agitating, followed by 3 changes of 100% Durcupan for 3 h each at RT agitating. Resin was polymerized at 80° C. for 3-4 days under vacuum. Sectioning was performed using AO/Reichert Ultramicrotome.

The nanoparticle morphology was characterized using high-resolution transmission electron microscopy (HR-TEM). The $CeO_2$ NPs were deposited on the carbon-coated copper grid for HRTEM analysis by the dip coating method. The HRTEM images of the as-prepared particles were obtained with a Philips (Tecnai Series) transmission electron microscope operating at 300 keV.

Electron Energy Loss Spectroscopy (EELS)

Sample preparation for EELS was an abbreviated protocol used for TEM preparation. Briefly, neurons were grown and treated as before but fixation was 2.5% glutaraldehyde in 0.1 M sodium cacodylate on ice for 30 min. Following 3×5 min rinses in ice-cold 0.1 M sodium cacodylate and 3 µM calcium chloride, cultures were postfixed in 0.5% osmium tetroxide with 3 µM calcium chloride in 0.1 M sodium cacodylate on ice for 20 min. Samples were dehydrated in ethanol series of ice-cold 20, 50, 70, 90% then 3 washes in 100% ethanol at RT for 1 min at final step. Samples were first infiltrated in 50% ethanol/50% Durcupan ACM for 30 min at RT agitating, followed by 3 changes of 100% Durcupan for at least 2 h at RT agitating. Resin was polymerized at 80° C. for 3-4 days under vacuum.

X-Ray Photoelectron Spectroscopy (XPS)

$CeO_2$ NPs were treated with $ONOO^-$ in 10 mM sodium phosphate buffer pH 7.4 and 50 µM DPTA. NPs were isolated by centrifugation at 20,000 RPM for 20 min, pellets dried and resuspended in same buffer. Samples were transferred onto silicon wafers and dried. The surface chemistry of the cerium oxide nanoparticles was studied using a Physical Electronics (5400 PHI ESCA) spectrometer with a monochromatic Al Kα X-ray source operated at 300 W and base pressure of $1 \times 10^{-9}$ Torr. The binding energy of the Au (4f7/2) at 84.0±0.1 eV was used to calibrate the binding energy scale of the spectrometer.

Statistics

Results were collected from at least 3 replicates and are expressed as mean±S.D. Statistical analysis from two populations were compared using two-tailed, paired Student's t-test or between experiments using two-tailed non-paired Student's t-test.

Dosage

The dose administered to an animal, particularly a human, in accordance with the present invention should be sufficient to affect the desired response in the animal over a reasonable time frame. One skilled in the art will recognize that dosage will depend upon a variety of factors, including the strength of the particular compositions employed, the age, species, condition, and body weight of the animal. The size of the dose also will be determined by the route, timing and frequency of administration as well as the existence, nature, and extent of any adverse side effects that might accompany the administration of a particular composition and the desired physiological effect. It will be appreciated by one of ordinary skill in the art that various conditions or desired results, may require prolonged treatment involving multiple administrations.

Suitable doses and dosage regimens can be determined by conventional range-finding techniques known to those of ordinary skill in the art. Generally, treatment is initiated with smaller dosages, which are less than the optimum dose of the compound. Thereafter, the dosage is increased by small increments until the optimum effect under the circumstances is reached.

As used herein, by the term "effective amount," "amount effective," "therapeutically effective amount," or the like, it is meant an amount effective at dosages and for periods of time necessary to achieve the desired result. The amount of the compound of the invention administered per dose or the total amount administered per day may be predetermined or it may be determined on an individual patient basis by taking into consideration numerous factors, including the nature and severity of the patient's condition, the condition being treated, the age, weight, and general health of the patient, the tolerance of the patient to the compound, the route of administration, pharmacological considerations such as the activity, efficacy, pharmacokinetics and toxicology profiles of the compound and any secondary agents being administered, and the like. Patients undergoing such treatment will typically be monitored on a routine basis to determine the effectiveness of therapy. Continuous monitoring by the physician will insure that the optimal amount of the compound of the invention will be administered at any given time, as well as facilitating the determination of the duration of treatment. This is of particular value when secondary agents are also being administered, as their selection, dosage, and duration of therapy may also require adjustment. In this way, the treatment regimen and dosing schedule can be adjusted over the course of therapy so that the lowest amount of compound that exhibits the desired effectiveness is administered and, further, that administration is continued only so long as is necessary to successfully achieve the optimum effect.

Pharmaceutical Compositions

As used herein, a "composition," "pharmaceutical composition" "therapeutic composition" or "therapeutic agent" all include a composition comprising at least cerium oxide nanoparticles. Optionally, the "composition," "pharmaceutical composition" "therapeutic composition" or "therapeutic agent" further comprises pharmaceutically acceptable diluents or carriers. In the case of an interfering molecule, for example, the interfering molecule may be combined with one or more pharmaceutically acceptable diluents, such as phosphate-buffered saline, for example. As used herein, a pharmaceutical composition particularly refers to a composition comprising at least a cerium oxide nanoparticle that is intended to be administered to a subject as described herein.

Various embodiments of the invention are foreseen to have valuable application as constituents of pharmaceutical preparations to treat various conditions generally defined as pathologies. Accordingly, embodiments of the invention also comprise pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, acetyl alcohol and cellulose acetate. The compositions may be contained in a vial, sponge, syringe, tube, or other suitable container.

As used herein, the terms "subject" and "patient" are used interchangeably. As used herein, the term "subject" refers to an animal, preferably a mammal such as a non-primate (e.g., cows, pigs, horses, cats, dogs, rats etc.) and a primate (e.g., monkey and human), and most preferably a human.

As used herein, the terms "treating" or "treatment" or "alleviation" refers to both therapeutic treatment and prophylactic or preventative measures, wherein the object is to prevent or slow down (lessen) the targeted pathologic condition or disorder.

As used herein, the term "administering" or "administration" includes but is not limited to oral or intravenous administration by liquid, capsule, tablet, or spray. Administration may be by injection, whether intramuscular, intravenous, intraperitoneal or by any parenteral route. Parenteral administration can be by bolus injection or by continuous infusion. Formulations for injection may be presented in unit dosage form, for example, in ampoules or in multi-dose containers with an added preservative. The compositions may take the form of suspensions, solutions or emulsions in oily or aqueous vehicles and may contain formulatory agents such as suspending, stabilizing and/or dispersing agents. Alternatively the compositions may be in powder form (e.g., lyophilized) for constitution with a suitable vehicle, for example sterile pyrogen-free water, before use. Compositions may be delivered to a subject by inhalation by any presently known suitable technique including a pressurized aerosol spray, where the dosage unit may be controlled using a valve to deliver a metered amount.

Administration by capsule and cartridges containing powder mix of the composition can be used in an inhaler or insufflator to deliver the particles to the subject. Still other routes of administration which may be used include buccal, urethral, vaginal, or rectal administration, topical administration in a cream, lotion, salve, emulsion, or other fluid may also be used.

It should be borne in mind that all patents, patent applications, patent publications, technical publications, scientific publications, and other references referenced herein are hereby incorporated by reference in this application in order to more fully describe the state of the art to which the present invention pertains.

Reference to particular buffers, media, reagents, cells, culture conditions and the like, or to some subclass of same, is not intended to be limiting, but should be read to include all such related materials that one of ordinary skill in the art would recognize as being of interest or value in the particular context in which that discussion is presented. For example, it is often possible to substitute one buffer system or culture medium for another, such that a different but known way is used to achieve the same goals as those to which the use of a suggested method, material or composition is directed.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the following definitions are provided.

While a number of embodiments of the present invention have been shown and described herein in the present context, such embodiments are provided by way of example only, and not of limitation. Numerous variations, changes and substitutions will occur to those of skill in the art without materially departing from the invention herein. For example, the present invention need not be limited to best mode disclosed herein, since other applications can equally benefit from the teachings of the present invention. Also, in the claims, means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

REFERENCES

1. Bossy-Wetzel E, Schwarzenbacher R, & Lipton S A (2004) Molecular pathways to neurodegeneration. (Translated from eng) *Nat Med* 10 Suppl:S2-9 (in eng).
2. Ferri C P, et al. (2005) Global prevalence of dementia: a Delphi consensus study. (Translated from eng) *Lancet* 366(9503):2112-2117 (in eng).
3. Markesbery W R (1997) Oxidative stress hypothesis in Alzheimer's disease. (Translated from eng) *Free Radic Biol Med* 23(1):134-147 (in eng).
4. Pacher P, Beckman J S, & Liaudet L (2007) Nitric oxide and peroxynitrite in health and disease. (Translated from eng) *Physiol Rev* 87(1):315-424 (in eng).
5. Barsoum M J, et al. (2006) Nitric oxide-induced mitochondrial fission is regulated by dynamin-related GTPases in neurons. (Translated from eng) *EMBO J* 25(16):3900-3911 (in eng).
6. Boczkowski J, et al. (2001) Peroxynitrite-mediated mitochondrial dysfunction. (Translated from eng) *Biol Signals Recept* 10(1-2):66-80 (in eng).
7. Smith M A, Richey Harris P L, Sayre L M, Beckman J S, & Perry G (1997) Widespread peroxynitrite-mediated damage in Alzheimer's disease. (Translated from eng) *J Neurosci* 17(8):2653-2657 (in eng).
8. Texel S J & Mattson M P (2011) Impaired adaptive cellular responses to oxidative stress and the pathogenesis of Alzheimer's disease. (Translated from eng) *Antioxid Redox Signal* 14(8):1519-1534 (in eng).
9. Shankar G M, et al. (2007) Natural oligomers of the Alzheimer amyloid-beta protein induce reversible synapse loss by modulating an NMDA-type glutamate receptor-dependent signaling pathway. (Translated from eng) *J Neurosci* 27(11):2866-2875 (in eng).
10. Reynolds M R, et al. (2006) Tau nitration occurs at tyrosine 29 in the fibrillar lesions of Alzheimer's disease and other tauopathies. (Translated from eng) *J Neurosci* 26(42):10636-10645 (in eng).
11. Reyes J F, et al. (2008) A possible link between astrocyte activation and tau nitration in Alzheimer's disease. (Translated from English) *Neurobiol Dis* 31(2):198-208 (in English).
12. Cadenas E & Boveris A (2005) Mitochondrial Free Radical Production, Antioxidant Defenses and Cell Signaling. *Reactions, Processes*, The Handbook of Environmental Chemistry, ed Grune T (Springer Berlin/Heidelberg), Vol 2O, pp 615-643.
13. Mattson M P, Gleichmann M, & Cheng A (2008) Mitochondria in neuroplasticity and neurological disorders. (Translated from eng) *Neuron* 60(5):748-766 (in eng).
14. Rabkin S W & Klassen S S (2008) Metalloporphyrins as a therapeutic drug class against peroxynitrite in cardiovascular diseases involving ischemic reperfusion injury. (Translated from eng) *Eur J Pharmacol* 586(1-3):1-8 (in eng).
15. Rong Y, Doctrow S R, Tocco G, & Baudry M (1999) EUK-134, a synthetic superoxide dismutase and catalase mimetic, prevents oxidative stress and attenuates kainate-induced neuropathology. (Translated from eng) *Proc Natl Acad Sci USA* 96(17):9897-9902 (in eng).
16. Sharpe M A, Ollosson R, Stewart V C, & Clark J B (2002) Oxidation of nitric oxide by oxomanganese-salen complexes: a new mechanism for cellular protection by superoxide dismutase/catalase mimetics. (Translated from eng) *Biochem J* 366(Pt 1):97-107 (in eng).
17. van Empel V P, et al. (2006) EUK-8, a superoxide dismutase and catalase mimetic, reduces cardiac oxidative stress and ameliorates pressure overload-induced heart failure in the harlequin mouse mutant. (Translated from eng) *J Am Coll Cardiol* 48(4):824-832 (in eng).
18. Celardo I, Pedersen J Z, Traversa E, & Ghibelli L (2011) Pharmacological potential of cerium oxide nanoparticles. (Translated from eng) *Nanoscale* 3(4):1411-1420 (in eng).
19. Chen J, Patil S, Seal S, & McGinnis J F (2006) Rare earth nanoparticles prevent retinal degeneration induced by intracellular peroxides. (Translated from eng) *Nat Nanotechnol* 1(2):142-150 (in eng).
20. Karakoti A, Singh S, Dowding J M, Seal S, & Self W T (2010) Redox-active radical scavenging nanomaterials. (Translated from eng) *Chem Soc Rev* 39(11):4422-4432 (in eng).
21. Heckert E G, Karakoti A S, Seal S, & Self W T (2008) The role of cerium redox state in the SOD mimetic activity of nanoceria. (Translated from eng) *Biomaterials* 29(18):2705-2709 (in eng).
22. Korsvik C, Patil S, Seal S, & Self W T (2007) Superoxide dismutase mimetic properties exhibited by vacancy engineered ceria nanoparticles. (Translated from English) *Chem Commun* (10):1056-1058 (in English).
23. Pirmohamed T, et al. (2010) Nanoceria exhibit redox state-dependent catalase mimetic activity. (Translated from eng) *Chem Commun (Camb)* 46(16):2736-2738 (in eng).
24. Anonymous (2009) Cerium Oxide Nanoparticles Trigger Neuronal Survival in a Human Alzheimer Disease Model By Modulating BDNF Pathway. *Current Nanoscience* 5:167-176.
25. Das M, et al. (2007) Auto-catalytic ceria nanoparticles offer neuroprotection to adult rat spinal cord neurons. (Translated from eng) *Biomaterials* 28(10):1918-1925 (in eng).
26. Schubert D, Dargusch R, Raitano J, & Chan S W (2006) Cerium and yttrium oxide nanoparticles are neuroprotective. (Translated from eng) *Biochem Biophys Res Commun* 342(1):86-91 (in eng).
27. Hardas S S, et al. (2010) Brain distribution and toxicological evaluation of a systemically delivered engineered nanoscale ceria. (Translated from eng) *Toxicol Sci* 116(2):562-576 (in eng).
28. Hirst S M, et al. (2011) Bio-distribution and in vivo antioxidant effects of cerium oxide nanoparticles in mice. (Translated from Eng) *Environ Toxicol* (in Eng).
29. Beckman J S (2009) Understanding peroxynitrite biochemistry and its potential for treating human diseases. (Translated from eng) *Arch Biochem Biophys* 484(2):114-116 (in eng).
30. Liot G, et al. (2009) Complex II inhibition by 3-NP causes mitochondrial fragmentation and neuronal cell death via an NMDA- and ROS-dependent pathway. (Translated from eng) *Cell Death Differ* 16(6):899-909 (in eng).
31. Viera L, Ye Y Z, Estevez A G, & Beckman J S (1999) Immunohistochemical methods to detect nitrotyrosine. (Translated from eng) *Methods Enzymol* 301:373-381 (in eng).
32. Patil S, Kuiry S C, Seal S, & Vanfleet R (2002) Synthesis of Nanocrystalline Ceria Particles for High Temperature Oxidation Resistant Coating. *Journal of Nanoparticle Research* 4(5):433-438.

33. Mailander V & Landfester K (2009) Interaction of nanoparticles with cells. (Translated from eng) *Biomacromolecules* 10(9):2379-2400 (in eng).
34. Vincent A, et al. (2009) Protonated nanoparticle surface governing ligand tethering and cellular targeting. (Translated from eng) *ACS Nano* 3(5):1203-1211 (in eng).
35. Limbach L K, et al. (2005) Oxide nanoparticle uptake in human lung fibroblasts: effects of particle size, agglomeration, and diffusion at low concentrations. (Translated from eng) *Environ Sci Technol* 39(23):9370-9376 (in eng).
36. Owens D E, 3rd & Peppas N A (2006) Opsonization, biodistribution, and pharmacokinetics of polymeric nanoparticles. (Translated from eng) *Int J Pharm* 307(1):93-102 (in eng).
37. Radi R (1996) Kinetic analysis of reactivity of peroxynitrite with biomolecules. (Translated from eng) *Methods Enzymol* 269:354-366 (in eng).
38. Lymar S V & Hurst J K (1995) Rapid reaction between peroxonitrite ion and carbon dioxide: Implications for biological activity. *Journal of the American Chemical Society* 117(34):8867-8868.
39. Pompella A, Visvikis A, Paolicchi A, De Tata V, & Casini A F (2003) The changing faces of glutathione, a cellular protagonist. (Translated from eng) *Biochem Pharmacol* 66(8):1499-1503 (in eng).
40. Setsukinai K, Urano Y, Kakinuma K, Majima H J, & Nagano T (2003) Development of novel fluorescence probes that can reliably detect reactive oxygen species and distinguish specific species. (Translated from eng) *J Biol Chem* 278(5):3170-3175 (in eng).
41. Whiteman M & Halliwell B (1996) Protection against peroxynitrite-dependent tyrosine nitration and alpha 1-antiproteinase inactivation by ascorbic acid. A comparison with other biological antioxidants. (Translated from eng) *Free Radic Res* 25(3):275-283 (in eng).
42. Radi R, Cassina A, & Hodara R (2002) Nitric oxide and peroxynitrite interactions with mitochondria. (Translated from eng) *Biol Chem* 383(3-4):401-409 (in eng).
43. Kumar A, Singh R L, & Babu G N (2010) Cell death mechanisms in the early stages of acute glutamate neurotoxicity. (Translated from eng) *Neurosci Res* 66(3):271-278 (in eng).
44. Kumar A, Singh R L, & Babu G N (Cell death mechanisms in the early stages of acute glutamate neurotoxicity. (Translated from eng) *Neurosci Res* 66(3):271-278 (in eng).
45. Radi R, Cassina A, Hodara R, Quijano C, & Castro L (2002) Peroxynitrite reactions and formation in mitochondria. (Translated from eng) *Free Radic Biol Med* 33(11):1451-1464 (in eng).
46. Selkoe D J (2004) Cell biology of protein misfolding: the examples of Alzheimer's and Parkinson's diseases. (Translated from eng) *Nat Cell Biol* 6(11):1054-1061 (in eng).
47. Kubo T, Nishimura S, Kumagae Y, & Kaneko I (2002) In vivo conversion of racemized beta-amyloid ([D-Ser 26]A beta 1-40) to truncated and toxic fragments ([D-Ser 26]A beta 25-35/40) and fragment presence in the brains of Alzheimer's patients. (Translated from eng) *J Neurosci Res* 70(3):474-483 (in eng).
48. Esposito C, et al. (2006) Exploring interaction of β-amyloid segment (25-35) with membrane models through paramagnetic probes. *Journal of Peptide Science* 12(12):766-774.
49. Millucci L, Raggiaschi R, Franceschini D, Terstappen G, & Santucci A (2009) Rapid aggregation and assembly in aqueous solution of A beta (25-35) peptide. (Translated from eng) *J Biosci* 34(2):293-303 (in eng).
50. Cho D H, et al. (2009) S-nitrosylation of Drp1 mediates beta-amyloid-related mitochondrial fission and neuronal injury. (Translated from eng) *Science* 324(5923):102-105 (in eng).
51. Glenner G G & Wong C W (1984) Alzheimer's disease: initial report of the purification and characterization of a novel cerebrovascular amyloid protein. (Translated from eng) *Biochem Biophys Res Commun* 120(3):885-890 (in eng).
52. Miranda S, et al. (2000) The role of oxidative stress in the toxicity induced by amyloid [beta]-peptide in Alzheimer's disease. *Progress in Neurobiology* 62(6):633-648.
53. Kayed R, et al. (2003) Common structure of soluble amyloid oligomers implies common mechanism of pathogenesis. (Translated from eng) *Science* 300(5618):486-489 (in eng).
54. Pietraforte D, Salzano A M, Marino G, & Minetti M (2003) Peroxynitrite-dependent modifications of tyrosine residues in hemoglobin. Formation of tyrosyl radical(s) and 3-nitrotyrosine. (Translated from eng) *Amino Acids* 25(3-4):341-350 (in eng).
55. Radi R, Peluffo G, Alvarez M N, Naviliat M, & Cayota A (2001) Unraveling peroxynitrite formation in biological systems. (Translated from eng) *Free Radic Biol Med* 30(5):463-488 (in eng).
56. Ye Y Z, Strong M, Huang Z Q, & Beckman J S (1996) Antibodies that recognize nitrotyrosine. (Translated from eng) *Methods Enzymol* 269:201-209 (in eng).
57. Besancon E, Guo S, Lok J, Tymianski M, & Lo E H (2008) Beyond NMDA and AMPA glutamate receptors: emerging mechanisms for ionic imbalance and cell death in stroke. (Translated from eng) *Trends Pharmacol Sci* 29(5):268-275 (in eng).
58. Smith D G, Cappai R, & Barnham K J (2007) The redox chemistry of the Alzheimer's disease amyloid beta peptide. (Translated from eng) *Biochim Biophys Acta* 1768(8):1976-1990 (in eng).
59. Zhang Y J, Xu Y F, Chen X Q, Wang X C, & Wang J Z (2005) Nitration and oligomerization of tau induced by peroxynitrite inhibit its microtubule-binding activity. (Translated from English) *Febs Lett* 579(11):2421-2427 (in English).
60. Crow J P, et al. (1997) Superoxide dismutase catalyzes nitration of tyrosines by peroxynitrite in the rod and head domains of neurofilament-L. (Translated from eng) *J Neurochem* 69(5):1945-1953 (in eng).
61. Tohgi H, et al. (1999) Alterations of 3-nitrotyrosine concentration in the cerebrospinal fluid during aging and in patients with Alzheimer's disease. (Translated from eng) *Neurosci Lett* 269(1):52-54 (in eng).
62. Basso M, et al. (2009) Characterization of Detergent-Insoluble Proteins in ALS Indicates a Causal Link between Nitrative Stress and Aggregation in Pathogenesis. *PLoS One* 4(12):e8130.
63. Bishop A, et al. (2009) Differential sensitivity of oligodendrocytes and motor neurons to reactive nitrogen species: implications for multiple sclerosis. (Translated from eng) *J Neurochem* 109(1):93-104 (in eng).
64. Ischiropoulos H & Beckman J S (2003) Oxidative stress and nitration in neurodegeneration: cause, effect, or association? (Translated from eng) *J Clin Invest* 111(2):163-169 (in eng).

65. Torreilles F, Salman-Tabcheh S, Guerin M, & Torreilles J (1999) Neurodegenerative disorders: the role of peroxynitrite. (Translated from eng) *Brain Res Brain Res Rev* 30(2):153-163 (in eng).
66. Alkam T, et al. (2008) The extensive nitration of neurofilament light chain in the hippocampus is associated with the cognitive impairment induced by amyloid beta in mice. (Translated from eng) *J Pharmacol Exp Ther* 327 (1):137-147 (in eng).
67. Bossy-Wetzel E, Schwarzenbacher R, & Lipton S A (2004) Molecular pathways to neurodegeneration. (Translated from eng) *Nat Med* 10 Suppl:S2-9 (in eng).
68. Ferri C P, et al. (2005) Global prevalence of dementia: a Delphi consensus study. (Translated from eng) *Lancet* 366(9503):2112-2117 (in eng).
69. Markesbery W R (1997) Oxidative stress hypothesis in Alzheimer's disease. (Translated from eng) *Free Radic Biol Med* 23(1):134-147 (in eng).
70. American Psychiatric Association (2000). *Diagnostic and statistical manual of mental disorders: DSM-IV-TR* (4th Edition Text Revision ed.). Washington, D.C.: American Psychiatric Association.
71. Bonte F J, Harris T S, Hynan L S, Bigio E H, White C L (July 2006). "Tc-99m HMPAO SPECT in the differential diagnosis of the dementias with histopathologic confirmation". *Clin Nucl Med* 31 (7): 376-8.
72. Dougall N J, Bruggink S, Ebmeier K P (2004). "Systematic review of the diagnostic accuracy of 99mTc-HMPAO-SPECT in dementia". *Am J Geriatr Psychiatry* 12 (6): 554-70. Advances have led to the proposal of new diagnostic criteria.
73. De Meyer G, Shapiro F, Vanderstichele H, Vanmechelen E, Engelborghs S, De Deyn P P, Coart E, Hansson O, Minthon L, Zetterberg H, Blennow K, Shaw L, Trojanowski J Q (August 2010). "Diagnosis-Independent Alzheimer Disease Biomarker Signature in Cognitively Normal Elderly People". *Arch Neurol*. 67 (8): 949-56.
74. Martinez-Ruiz A, Cadenas S, Lamas S. Nitric oxide signaling: classical, less classical, and nonclassical mechanisms. *Free Radic Biol Med*. 2011; 51: 17-29.
75. Stamler J S, Lamas S, Fang F C. Nitrosylation. the prototypic redox-based signaling mechanism. *Cell*. 2001; 106(6): 675-683.
76. Ghatan S, Lamer S, Kinoshita Y, Hetman M, Patel L, Xia Z, et al. p38 MAP kinase mediates bax translocation in nitric oxide-induced apoptosis in neurons. *J Cell Biol*. 2000; 150: 335-347.
77. Knott A B, Perkins G, Schwarzenbacher R, Bossy-Wetzel E. Mitochondrial fragmentation in neurodegeneration. *Nat Rev Neurosci*. 2008; 9: 505-518.
78. Manczak M, Calkins M J, Reddy P H. Impaired mitochondrial dynamics and abnormal interaction of amyloid beta with mitochondrial protein Drp1 in neurons from patients with Alzheimer's disease: implications for neuronal damage. *Hum Mol Genet*. 2011; 20: 2495-2509.
79. Ikiz B, Przedborski S. A sequel to the tale of p25/Cdk5 in neurodegeneration. *Neuron*. 2008; 60: 731-732.
80. Swerdlow R H. Pathogenesis of Alzheimer's disease. Clin Interv Aging. 2007; 2: 347-359.
81. Chaturvedi R K, Beal M F. Mitochondrial approaches for neuroprotection. Ann N Y Acad Sci. 2008; 1147: 395-412.
82. Estevez A Y, Pritchard S, Harper K, Aston J W, Lynch A, Lucky J J, et al. Neuroprotective mechanisms of cerium oxide nanoparticles in a mouse hippocampal brain slice model of ischemia. Free Radic Biol Med. 2011; 51: 1155-1163.
83. Song W, Bossy B, Martin O J, Hicks A, Lubitz S, Knott A B, et al. Assessing mitochondrial morphology and dynamics using fluorescence wide-field microscopy and 3D image processing. Methods. 2008; 46: 295-303.
84. Bossy-Wetzel E, Talantova M V, Lee W D, Scholzke M N, Harrop A, Mathews E, et al. Crosstalk between nitric oxide and zinc pathways to neuronal cell death involving mitochondrial dysfunction and p38-activated K+ channels. Neuron. 2004; 41: 351-365.
85. Knott A B, Bossy-Wetzel E. Impact of nitric oxide on metabolism in health and age-related disease. Diabetes Obes Metab. 2010; 12: 126-133.
86. Bossy B, Petrilli A, Klinglmayr E, Chen J, Lutz-Meindl U, Knott A B, et al. S-Nitrosylation of DRP1 does not affect enzymatic activity and is not specific to Alzheimer's disease. J Alzheimers Dis. 2010; 20 Suppl 2: S513-526.
87. Wang X, Su B, Lee H G, Li X, Perry G, Smith M A, et al. Impaired balance of mitochondrial fission and fusion in Alzheimer's disease. J Neurosci. 2009; 29: 9090-9103.
88. Taguchi N, Ishihara N, Jofuku A, Oka T, Mihara K. Mitotic phosphorylation of dynamin-related GTPase Drp1 participates in mitochondrial fission. J Biol Chem. 2007; 282: 11521-1152.
89. Yamano K, Youle R J. Coupling mitochondrial and cell division. Nat Cell Biol. 2011; 13: 1026-1027.
90. Nguyen M D, Mushynski W E, Julien J P. Cycling at the interface between neurodevelopment and neurodegeneration. Cell Death Differ. 2002; 9: 1294-1306.
91. Crews L, Masliah E. Molecular mechanisms of neurodegeneration in Alzheimer's disease. Hum Mol Genet. 2010; 19: R12-20.
92. Ikiz B, Przedborski S. A sequel to the tale of p25/Cdk5 in neurodegeneration. Neuron. 2008; 60: 731-732.
93. Qu J, Nakamura T, Cao G, Holland E A, McKercher S R, Lipton S A. S-Nitrosylation activates Cdk5 and contributes to synaptic spine loss induced by beta-amyloid peptide. Proc Natl Acad Sci USA. 2011; 108: 14330-14335.
94. Knott A B, Bossy-Wetzel E. Nitric oxide in health and disease of the nervous system. Antioxid Redox Signal. 2009; 11: 541-554.
95. Swerdlow R H, Burns J M, Khan S M. The Alzheimer's disease mitochondrial cascade hypothesis. J Alzheimers Dis. 2010; 20 Suppl 2: S265-279.
96. Cho D-H, Nakamura T, Fang J, Cieplak P, Godzik A, Gu Z, et al. S-Nitrosylation of Drp1 Mediates β-Amyloid-Related Mitochondrial Fission and Neuronal Injury. Science. 2009; 324: 102-105.
97. Chan D C. Mitochondria: dynamic organelles in disease, aging, and development. Cell. 2006; 125: 1241-1252.
98. Song W, Bossy B, Martin O J, Hicks A, Lubitz S, Knott A B, et al. Assessing mitochondrial morphology and dynamics using fluorescence wide-field microscopy and 3D image processing. Methods. 2008; 46: 295-303.

What is claimed is:

1. A method of treating a subject identified as at risk of developing a neurodegenerative disease, comprising:
administering a therapeutically effective amount of cerium oxide nanoparticles (CeO$_2$NPs) to the subject, wherein the cerium oxide nanoparticles scavenge reactive oxygen species (ROS) and reactive nitrogen species (RNS) in the subject; wherein the cerium oxide nanoparticles comprise more Ce$^{3+}$ than Ce$^{4+}$; wherein the patient at risk exhibits symptoms comprising at least one of the following: amyloid plaques in the brain or increased beta-amyloid deposits, neurofibrillary tangles (NFTs) in the brain, an atrophic brain region, atrophy of the hippocampus, increase in brain ventricle size, elevated levels of tau and/or amyloid beta proteins in cerebral spinal fluid, loss of function in the temporal lobe, cognitive deficiencies in memory, language, perceptual skills, attention, constructive abilities, orientation, problem solving, and/or functional abilities.

2. The method of claim 1, wherein the RNS is peroxynitrite.

3. The method of claim 1, wherein the patient at risk exhibits at least two of said symptoms.

4. The method of claim 1, wherein the patient at risk exhibits symptoms comprising at least one of the following: reduced dopaminergic activity in the basal ganglia, death of dopaminergic neurons in the substantia nigra pars compacta, motor symptoms comprising Parkinsonian gait, tremors, rigidity, slowness of movement, postural instability, non-motor symptoms comprising autonomic dysfunction, neuropsychiatric problems, sensory problems and/or sleep-related difficulties.

5. The method of claim 1, wherein the patient at risk exhibits symptoms comprising at least two of the following: reduced dopaminergic activity in the basal ganglia, death of dopaminergic neurons in the substantia nigra pars compacta, motor symptoms comprising Parkinsonian gait, tremors, rigidity, slowness of movement, postural instability, non-motor symptoms comprising autonomic dysfunction, neuropsychiatric problems, sensory problems and/or sleep-related difficulties.

6. The method of claim 1, wherein the cerium oxide nanoparticles range between 1-5 nanometers in size.

7. The method of claim 1, wherein the cerium oxide nanoparticles range between 5-10 nanometers in size.

* * * * *